United States Patent [19]

Kaneko et al.

[11] Patent Number: 5,637,439
[45] Date of Patent: Jun. 10, 1997

[54] PHOTOGRAPHIC SILVER HALIDE PHOTOSENSITIVE MATERIAL AND METHOD FOR DEVELOPING THE SAME

[75] Inventors: Satoshi Kaneko; Kenji Hirata; Akira Tanaka, all of Tokyo, Japan; Reinhold Rüger, Rodermark, Germany

[73] Assignees: Mitsubishi Paper Mills Ltd., Tokyo, Japan; E. I. Du Pont de Nemours and Company, Wilmington, Del.

[21] Appl. No.: 551,961

[22] Filed: Nov. 2, 1995

[30] Foreign Application Priority Data

| Nov. 7, 1994 | [JP] | Japan | 6-272247 |
| Jan. 17, 1995 | [JP] | Japan | 7-004996 |
| Apr. 26, 1995 | [JP] | Japan | 7-102448 |

[51] Int. Cl.⁶ .................................................. G03C 1/06
[52] U.S. Cl. ........................... 430/264; 430/413; 430/415; 430/434; 430/435; 430/440; 430/448; 430/598; 430/599; 430/600
[58] Field of Search ................................. 430/264, 413, 430/415, 434, 435, 440, 448, 598, 599, 600

[56] References Cited

U.S. PATENT DOCUMENTS

| 4,269,929 | 5/1981 | Northnagle | 430/264 |
| 4,385,108 | 5/1983 | Takagi et al. | 430/264 |
| 4,447,522 | 5/1984 | Hirano et al. | 430/448 |
| 4,851,321 | 7/1989 | Takagi et al. | 430/264 |
| 4,975,354 | 12/1990 | Machonkin et al. | 430/415 |
| 4,988,604 | 1/1991 | Machonkin et al. | 430/264 |
| 4,994,365 | 2/1991 | Looker et al. | 430/598 |
| 5,104,769 | 4/1992 | Looker et al. | 430/264 |
| 5,283,158 | 2/1994 | Onodera et al. | 430/264 |
| 5,478,696 | 12/1995 | Arai | 430/264 |

FOREIGN PATENT DOCUMENTS

| 60-140340 | 7/1985 | Japan. |
| 62-222241 | 9/1987 | Japan. |

OTHER PUBLICATIONS

Derwent Abstracts, JP-A-53 016 623, Feb. 15, 1978.
Derwent Abstracts, JP-A-53 020 921, Feb. 25, 1978.
Derwent Abstracts, JP-A-53 020 922, Feb. 25, 1978.
Derwent Abstracts, JP-A-53 049 429, May 4, 1978.
Derwent Abstracts, JP-A-53 066 732, Jun. 14, 1978.
Derwent Abstracts, JP-A-56 067 843, Jun. 8, 1981.
Derwent Abstracts, JP-A-57 099 635, Jun. 21, 1982.
Derwent Abstracts, JP-A-62 073 256, Apr. 3, 1987.
Derwent Abstracts, JP-A-62 275 247, Nov. 30, 1987.
Derwent Abstracts, JP-A-62 178 246, Aug. 5, 1987.
Derwent Abstracts, JP-A-62 180 361, Aug. 7, 1987.
Derwent Abstracts, JP-A-63 121 838, May 25, 1988.
Derwent Abstracts, JP-A-63 223 744, Sep. 19, 1988.
Derwent Abstracts, JP-A-63 253 357, Oct. 20, 1988.
Derwent Abstracts, JP-A-1 904 39, Apr. 6, 1989.
Derwent Abstracts, JP-A-1 105 943, Apr. 24, 1989.
Derwent Abstracts, JP-A-2 025 843, Jan. 29, 1990.
Derwent Abstracts, JP-A-2 120 736, May 8, 1990.
Derwent Abstracts, JP-A-2 000 037, Jan. 5, 1990.
Derwent Abstracts, JP-A-2 008 834, Jan. 12, 1990.
Derwent Abstracts, JP-A-3 184 039, Aug. 12, 1991.
Derwent Abstracts, JP-A-4 051 143, Feb. 19, 1992.
Derwent Abstracts, JP-A-60 179 734, Sep. 13, 1985.
Derwent Abstracts, JP-A-62 000 948, Jan. 6, 1987.
Derwent Abstracts, JP-A-56 106 244, Aug. 24, 1981.
Derwent Abstracts, JP-A-60 218 642, Nov. 1, 1985.
Derwent Abstracts, JP-A-61 267 759, Nov. 27, 1986.

(List continued on next page.)

*Primary Examiner*—Geraldine Letscher
*Attorney, Agent, or Firm*—Oblon, Spivak, McClelland, Maier & Neustadt, P.C.

[57] ABSTRACT

Negative images of super-high contrast can be formed by developing an exposed silver halide photographic photosensitive material in the presence of at least one compound selected from the compound of formula (1):

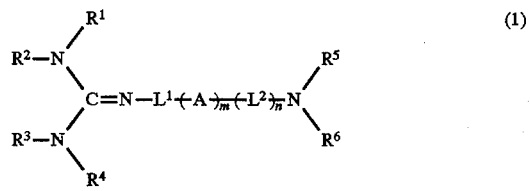

wherein $R^1$, $R^2$, $R^3$, $R^4$, $R^5$ and $R^6$ independently represent a hydrogen atom, an alkyl group, an aryl group or a heterocyclic group, $R^1$ and $R^2$, $R^3$ and $R^4$, $R^5$ and $R^6$, or $R^1$ and $R^3$, together with nitrogen atom to which they are attached, may form a ring; $L^1$ and $L^2$ independently represent an alkylene group, an arylene group or a repeated alkyleneoxy group having at least two repeated alkyleneoxy units, which groups may be optionally substituted; A represents an atom selected from hydrogen, carbon, nitrogen, oxygen and sulfur or a divalent linkage group constituted from these atoms; and m and n represent 0 or 1, and the compound of formula (2)

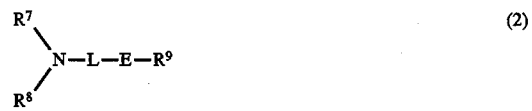

wherein $R^7$, $R^8$ and $R^9$ independently represent a hydrogen atom, an alkyl group, an aryl group or a heterocyclic group; $R^7$ and $R^8$ together with nitrogen atom to which they are attached, may form a ring; L represents an alkylene group, an arylene group or a repeated alkyleneoxy group having at least two repeated alkyleneoxy units, which groups may be substituted or unsubstituted; and E represents $-N(COR^{11})-$, $-N(CONR^{12}R^{13})-$, $-NR^{14}COCONR^{15}-$, $-N(COCONR^{16}R^{17})-$, $-N(SO_2R^{18})-$ or $-N(COOR^{19})-$, where $R^{11}-R^{19}$ independently represent a hydrogen atom, an alkyl group, an aryl group or a heterocyclic group; and $R^{12}$ and $R^{13}$ or $R^{16}$ and $R^{17}$ together with nitrogen atom to which they are attached, may form a ring, with the proviso that when E represents $-N(COR^{11})-$, $-N(CONR^{12}R^{13})-$, $-N(SO_2R^{18})-$ or $-N(COOR^{19})-$, $R^9$ is not a hydrogen atom.

17 Claims, No Drawings

OTHER PUBLICATIONS

Derwent Abstracts, JP-A-60-140 340, Jul. 25, 1985.
Derwent Abstracts, JP-A-62-222241, Sep. 30, 1987.
Derwent Abstracts, JP-A-63 124 045, May 27, 1988.

Patent Abstracts of Japan, vol. 13, No. 37, Jan. 27, 1989, JP-A-63 234 244, Sep. 29, 1988.

Patent Abstracts of Japan, vol. 4, No. 142, Oct. 7, 1980, JP-A-55 090 940, Jul. 10, 1980.

5,637,439

PHOTOGRAPHIC SILVER HALIDE PHOTOSENSITIVE MATERIAL AND METHOD FOR DEVELOPING THE SAME

FIELD OF THE INVENTION

This invention relates to a photographic silver halide photosensitive material and a method for forming a super-high contrast negative image using the photosensitive material and more particularly, to a photographic silver halide photosensitive material used for photomechanical process.

BACKGROUND OF THE INVENTION

Recently, color prints and complicated prints have been increasingly desired in the field of photomechanical process. Accordingly, demand for improvement of quality and stability of silver halide photosensitive materials used for printing (hereinafter referred to as "printing photosensitive material") which are intermediate media in printing increases steadily. Hitherto, general printing photosensitive materials have been imparted with so-called lith developability for obtaining prints of high quality. However, in the lith development, it is mechanically impossible to allow the developer to contain a sulfite ion at a high concentration as a preservative and it is well known for one skilled in the art that the developer is considerably low in stability. Some proposals have been made on the techniques to solve the instability of lith development and to obtain images having a contrast as high as that obtained by lith development. These are disclosed in patent publications. For example, use of hydrazine compounds to obtain high-contrast images is disclosed in Japanese Patent Kokai Nos. 53-16623, 53-20921, 53-20922, 53-49429, 53-66732, 55-90940, 56-67843, 57-99635, 62-73256, 62-275247, 62-178246, 62-180361, 63-121838, 63-223744, 63-234244, 63-253357, 64-90439, 1-105943, 2-25843, 2-120736, 2-37, 2-8834, 3-184039 and 4-51143. It is necessary for obtaining high-contrast images that the developers containing the hydrazine compounds have a relatively high pH value. The developers having a high pH value suffer from the problems that they absorb carbon dioxide in the air to cause decrease of pH and are not necessarily sufficient in stability against air oxidation to result in reduction of service life.

For forming high-contrast images with developers of lower pH value to solve these problems, attempts have been made to render more active the hydrazine derivatives used, as disclosed in Japanese Patent Kokai Nos. 60-179734 and 62-948 and U.S. Pat. Nos. 4,385,108, 4,269,929, 4,988,604, 4,994,365 and 5,104,769. However, there is a limit in increasing the contrast of images using developers of low pH only by improving the hydrazine derivatives. Therefore, contrast promoters have been developed. It is known to add secondary or tertiary amino compounds to developers as described in Japanese Patent Kokai Nos. 56-106244, 60-218642 and 61-267759 and to also add the amino compounds to photosensitive materials as disclosed in Japanese Patent Kokai Nos. 60-140340, 62-222241 and 63-124045 and U.S. Pat. No. 4,975,354. However, these methods still have the problems that no satisfactorily high contrast can be obtained, the compounds must be used in a large amount and photographic performances change greatly when compositions of the developers change after running or owing to air oxidation. Under the circumstances, more effective promoters have been desired.

SUMMARY OF THE INVENTION

An object of this invention is to provide a photosensitive material which can give images of high contrast and high density with a stable developer having a low pH value.

Another object of the invention is to provide a photosensitive material for making printing plates which contains an effective promoter showing an action to promote enhancement of contrast with addition of it in a small amount.

A further object of the invention is to provide a photographic silver halide photosensitive material which is less in change of photographic performance due to the change in composition of the developers.

Other and further objects, features and advantages of the invention will appear from the following description.

DETAILED DESCRIPTION OF THE INVENTION

In accordance with the invention, there is provided a method for developing a photographic silver halide photosensitive material which comprises developing an exposed photographic silver halide photosensitive material in the presence of at least one compound selected from the compound of formula (1):

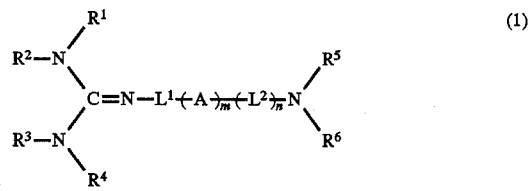

wherein $R^1$, $R^2$, $R^3$, $R^4$, $R^5$ and $R^6$ independently represent a hydrogen atom, an alkyl group, an aryl group or a heterocyclic group, $R^1$ and $R^2$, $R^3$ and $R^4$, $R^5$ and $R^6$, or $R^1$ and $R^3$, together with nitrogen atom to which they are attached, may form a ring; $L^1$ and $L^2$ independently represent an alkylene group, an arylene group or a repeated alkyleneoxy group having at least two repeated alkyleneoxy units, which groups may be optionally substituted; A represents an atom selected from hydrogen, carbon, nitrogen, oxygen and sulfur or a divalent linkage group constituted from these atoms; and m and n represent 0 or 1, and the compound of formula (2)

wherein $R^7$, $R^8$ and $R^9$ independently represent a hydrogen atom, an alkyl group, an aryl group or a heterocyclic group; $R^7$ and $R^8$ together with nitrogen atom to which they are attached, may form a ring; L represents an alkylene group, an arylene group or a repeated alkyleneoxy group having at least two repeated alkyleneoxy units, which groups may be optionally substituted; and E represents —N(COR$^{11}$)—, N(CONR$^{12}$R$^{13}$)—, —NR$^{14}$COCONR$^{15}$—, —N(COCONR$^{16}$R$^{17}$)—, —N(SO$_2$R$^{18}$)— or —N(COOR$^{19}$)—, where $R^{11}$-$R_{19}$ independently represent a hydrogen atom, an alkyl group, an aryl group or a heterocyclic group; and $R^{12}$ and $R^{13}$ or $R^{16}$ and $R^{17}$ together with nitrogen atom to which they are attached, may form a ring, with the proviso that only the case where E represents either —NR$^4$COCONR$^{15}$— or —N(COCONR$^{16}$R$^{17}$)—, $R^9$ is either a hydrogen atom or an alkyl group.

In the practice of the present invention, development of the photograpic silver halide photosensitive materials is conducted in the presence of at least one of the above compounds of formulae (1) and (2). The above compound can be incorporated in the photographic photosensitive material or in the developing system. It is essential that the above compound is present in during development of the exposed photosensitive material.

The compounds of formulas (1) and (2) which can be used as an effective super high contrast-promoting agent in the present invention are detailed below.

The alkyl groups represented by $R^1$, $R^2$, $R^3$, $R^4$, $R^5$ and $R^6$ in formula (1) include a substituted or unsubstituted $C_1$–$C_{30}$ alkyl which may be a straight, branched or cyclic alkyl. Examples of the unsubstituted alkyl groups include methyl, ethyl, n-propyl, isopropyl, n-butyl, isobutyl, tert butyl, pentyl, hexyl, cyclopentyl, cyclohexyl and n-decyl groups. Substituents in the substituted alkyl may include an aryl group such as phenyl and naphthyl; an alkenyl group such as vinyl, allyl and butenyl; an alkynyl group such as ethynyl; a heterocyclic group such as pyridyl, tetrahydropyranyl and sulforanyl; a hydroxy group; an alkoxy group such as methoxy, ethoxy, benzyloxy and polyethyleneoxyalkyl; an alkoxycarbonyl group such as ethoxycarbonyl and benzyloxycarbonyl; a carboxy group; a sulfo group; a halogen atom such as chlorine and bromine; a cyano group; an aryloxy group such as phenoxy and p-tolyloxy; an acyloxy group such as acetyloxy and propionyloxy; an acyl group such as acetyl, propionyl, benzoyl and mesyl; a carbamoyl group such as carbamoyl, N,N-dimethylcarbamoyl, morphorinocarbonyl and piperidinocarbonyl; a sulfamoyl group such as sulfamoyl, N,N-dimethylsulfamoyl, morphorinosulfonyl and piperidinosulfonyl; an acylamino group such as acetylamino, propionylamino and mesylamino; a sulfonamido group such as ethylsulfonamide and p-toluenesulfonamide; an ureido group such as methylureido and phenylureido, an amino group such as diethylamino.

The aryl groups represented by $R^1$, $R^2$, $R^3$, $R^4$, $R^5$ and $R^6$ in formula (1) include phenyl and naphtyl which may optionally be substituted. Examples of the substituents in the substituted aryl groups include an aryl group such as phenyl and naphthyl; an alkenyl group such as vinyl, allyl and butenyl; a alkynyl group such as ethynyl; an heterocyclic group such as pyridyl, tetrahydropyranyl and sulforanyl; a hydroxy group; an alkoxy group such as methoxy, ethoxy, benzyloxy and polyethyleneoxyalkyl; an alkoxycarbonyl group such as ethoxycarbonyl and benzyloxycarbonyl; a carboxy group; a sulfo group; a halogen atom such as chlorine and bromine; a cyano group, an aryloxy group such as phenoxy and p-tolyloxy; an acyloxy group such as acetyloxy and propionyloxy; an acyl group such as acetyl, propionyl, benzoyl and mesyl; a carbamoyl group such as carbamoyl, N,N-dimethylcarbamoyl, morphorinocarbonyl and piperidinocarbonyl; a sulfamoyl group such as sulfamoyl, N,N-dimethylsulfamoyl, morphorinosulfonyl and piperidinosulfonyl; an acylamino group such as acetylamino, propionylamino and methylamino; a sulfonamide group such as ethylsulfonamide and p-toluenesulfonamide; an ureido group such as methylureido and phenylureido; and an amino group such as diethylamino.

The heterocyclic groups represented by $R^1$, $R^2$, $R^3$, $R^4$, $R^5$ and $R^6$ in formula (1) include piperidyl, morphorinyl, furyl, thienyl, tetrahydropyranyl and pyridyl groups, which may optionally be substituted. Examples of the substituents in the substituted heterocyclic groups include an aryl group such as phenyl and naphthyl; an alkenyl group such as vinyl, allyl and butenyl; a alkynyl group such as ethynyl; an heterocyclic group such as pyridyl, tetrahydropyranyl and sulforanyl; a hydroxy group; an alkoxy group such as methoxy, ethoxy, benzyloxy and polyethyleneoxyalkyl; an alkoxycarbonyl group such as ethoxycarbonyl and benzyloxycarbonyl; a carboxy group; a sulfo group; a halogen atom such as chlorine and bromine; a cyano group; an aryloxy group such as phenoxy and p-tolyloxy; an acyloxy group such as acetyloxy and propionyloxy; an acyl group such as acetyl, propionyl, benzoyl and mesyl; a carbamoyl group such as carbamoyl, N,N-dimethylcarbamoyl, morphorinocarbonyl and piperidinocarbonyl; a sulfamoyl group such as sulfamoyl, N,N-dimethylsulfamoyl, morphorinosulfonyl and piperidinosulfonyl; an acylamino group such as acetylamino, propionylamino and mesylamino; a sulfonamide group such as ethylsulfonamide and p-toluenesulfonamide; an ureido group such as methylureido and phenylureido; and an amino group such as diethylamino.

Alternatively, $R^1$ and $R^2$, $R^3$ and $R^4$, $R^5$ and $R^6$, and $R^1$ and $R^3$ in formula (1), together with nitrogen atom to which they are attached, may form a heterocyclic ring. Examples of such heterocyclic rings may include a 5- to 7-member N-hetero cyclic, pyrrolidine, piperidine and perhydroazepin rings. These N-heterocyclic rings may optionally contain other hetero atoms such as N, O, and S, thus forming a saturated heterocyclic ring containing two hetero atoms such as imidazolidine, piperazine and morpholine rings.

The alkylene groups represented by $L^1$ and $L^2$ in formula (1) include a $C_1$–$C_{10}$ alkylene group such as methylene, ethylene and propylene, which groups may optionally be substituted. Examples of the substituents in the substituted alkylene groups include alkyl, aryl, alkoxy and hydroxy groups and halogen atoms.

The arylene groups represented by $L^1$ and $L^2$ include a phenylene group and a naphthylene group, which may be substituted. Examples of the substituents in the substituted arylene group include an aryl group such as phenyl and naphthyl; an alkenyl group such as vinyl, aliyl and butenyl; a alkynyl group such as ethynyl; an heterocyclic group such as pyridyl, tetrahydropyranyl and sulforanyl; a hydroxy group; an alkoxy group such as methoxy, ethoxy, benzyloxy and polyethyleneoxyalkyl; an alkoxycarbonyl group such as ethoxycarbonyl and benzyloxycarbonyl; a carboxy group; a sulfo group; a halogen atom such as chlorine and bromine; a cyano group; an aryloxy group such as phenoxy and p-tolyloxy; an acyloxy group such as acetyloxy and propionyloxy; an acyl group such as acetyl, propionyl, benzoyl and mesyl; a carbamoyl group such as carbamoyl, N,N-dimethylcarbamoyl, morphorinocarbonyl and piperidinocarbonyl; a sulfamoyl group such as sulfamoyl, N,N-dimethylsulfamoyl, morphorinosulfonyl and piperidinosulfonyl; an acylamino group such as acetylamino, propionylamino and mesylamino; a sulfonamide group such as ethylsulfonamide and p-toluenesulfonamide; an ureido group such as methylureido and phenylureido; an amino group such as diethylamino.

The repeated alkyleneoxy groups represented by $L^1$ and $L^2$ may include those having two or more alkyleneoxy repeating unit such as ethyleneoxy, propyleneoxy, butyleneoxy, i.e. ethyleneoxyethylenoxy, ethyleneoxyethyleneoxyethleneoxy, propyleneoxypropyleneoxy, propyleneoxypropyleneoxypropyleneoxy or the like.

The divalent linking groups represented by A in formula (1) include —CONR$^{11}$—, OCONR$^{11}$—, NR$^{11}$COCONR$^{11}$—, —NR$^{11}$COO—, —COO—, —OCO—, —CO—, —NR$^{11}$CO—, —SO$_2$NR$^{11}$—, —NR$^{11}$SO$_2$—, —SO$_2$—, —O—, —S—, —NR$^{11}$—wherein R$^{11}$ may be a hydrogen atom, an alkyl group, an acyl group or an alkylsulfonyl group.

In formula (1), m and n represent 0 or 1.

The compounds of formula (1) may form a salt such as a salt with hydrochloric acid or p-toluenesulfonic acid.

Representative examples of the compounds of formula (1) are given below, but not limiting thereto.
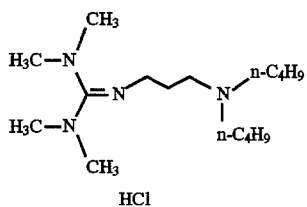
A-1
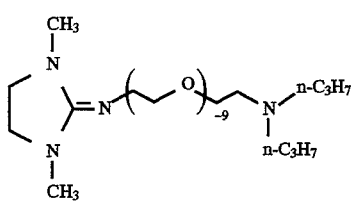
A-2
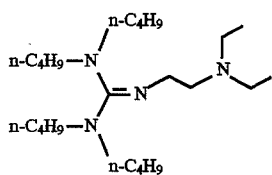
A-3
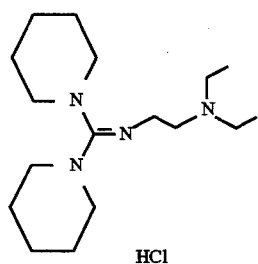
A-4
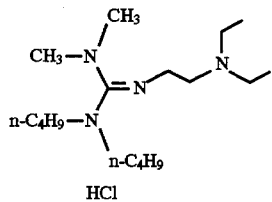
A-5
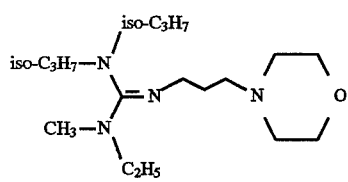
A-6
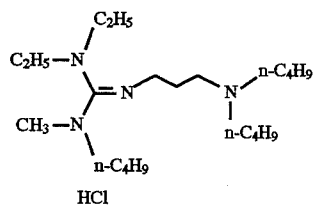
A-7
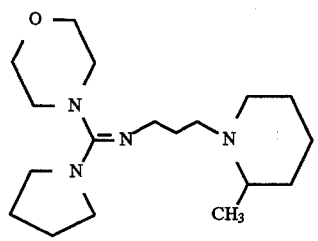
A-8
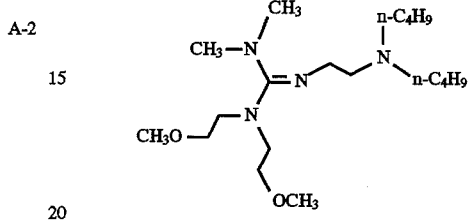
A-9
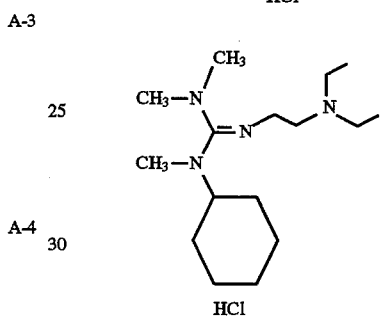
A-10
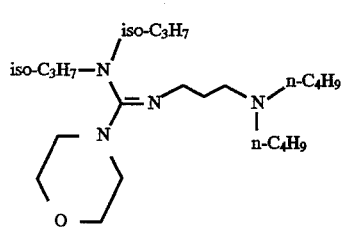
A-11
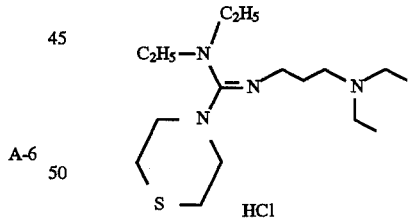
A-12
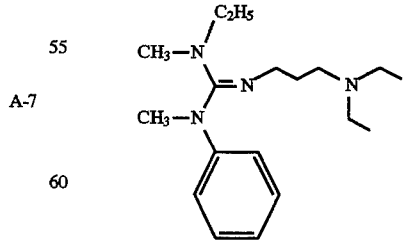
A-13

-continued
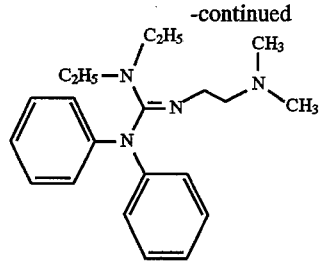
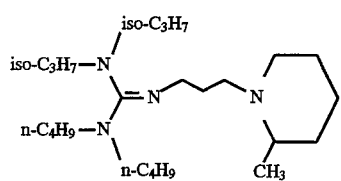
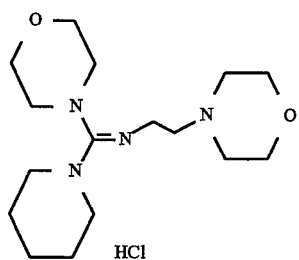
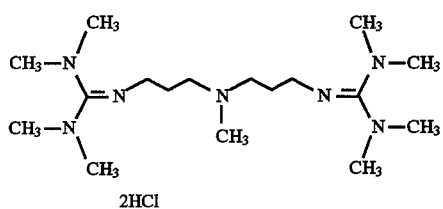
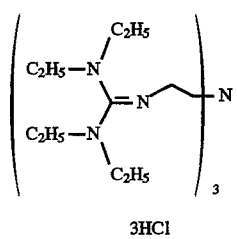
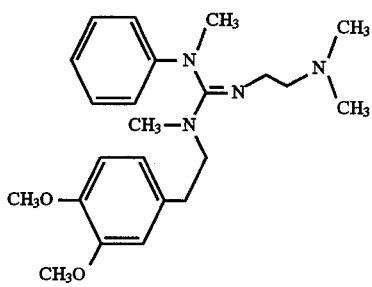
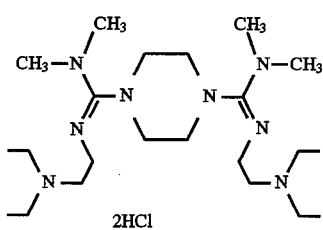
-continued
A-14
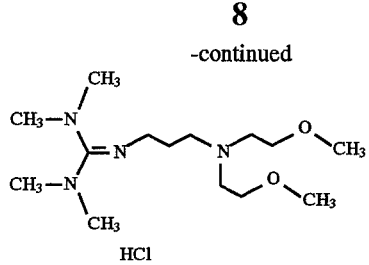
A-15
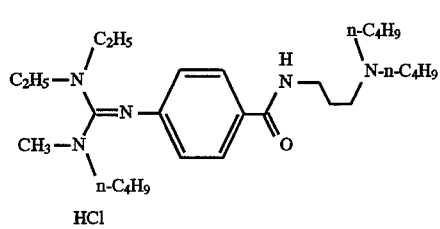
A-16
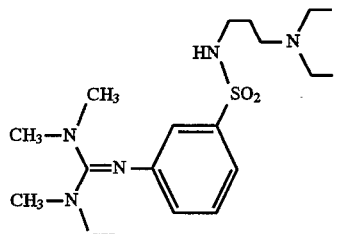
A-17
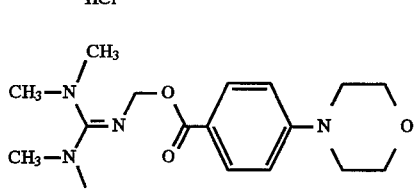
A-18
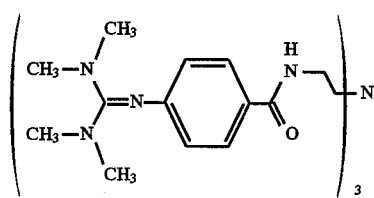
A-19
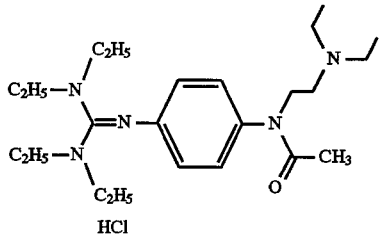
A-20
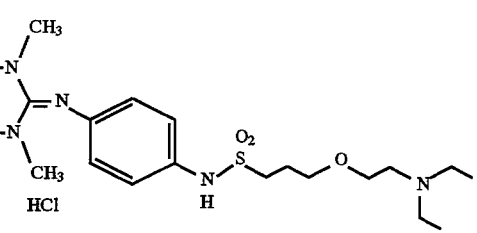
A-21
A-22
A-23
A-24
A-25
A-26
A-27

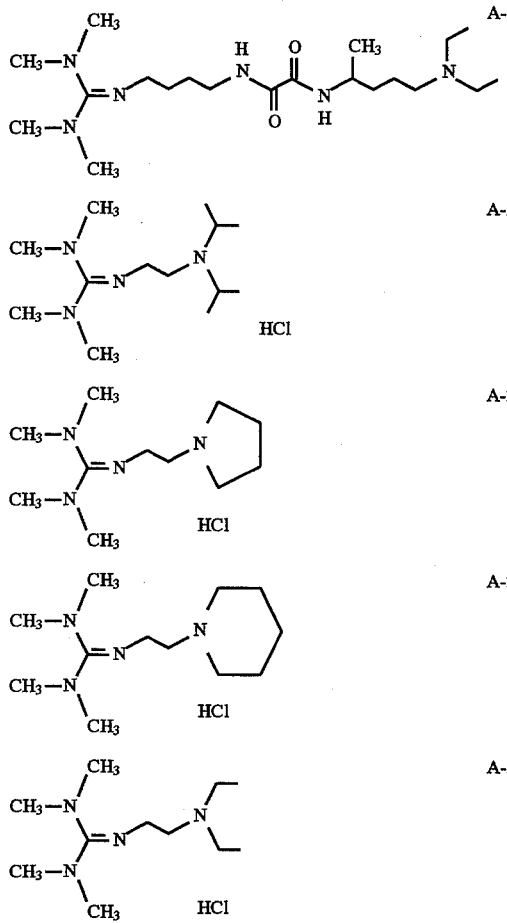

The alkyl groups represented by $R^7$, $R^8$ and $R^9$ include a substituted or unsubstituted alkyl group of 1–30 carbon atoms, which may be straight, branched or cyclic. Examples of the unsubstituted alkyl groups include methyl, ethyl, n-propyl, iso-propyl, hexyl, cyclohexyl and n-decyl. Examples of the substituents in the substituted alkyl groups include aryl groups such as phenyl and naphthyl groups; alkenyl groups such as vinyl, allyl and butenyl groups; alkynyl groups such as ethynyl group; heterocyclic groups such as pyridyl, tetrahydropyranyl and sulforanyl groups; hydroxyl group; alkoxy groups such as methoxy, ethoxy, benzyloxy and polyethyleneoxyalkyl groups; alkoxycarbonyl groups such as ethoxycarbonyl and benzyloxycarbonyl groups; carboxyl group; sulfo group; halogen atoms such as chlorine and bromine atoms; cyano group; aryloxy groups such as phenoxy and p-tolyloxy groups; acyloxy groups such as acetyloxy and propionyloxy groups; acyl groups such as acetyl, propionyl, benzoyl and mesyl groups; carbamoyl groups such as carbamoyl, N,N-dimethylcarbamoyl, morpholinocarbonyl and piperidinocarbonyl groups; sulfamoyl groups such as sulfamoyl, N,N-dimethylsulfamoyl, morpholinosulfonyl and piperidinosulfonyl groups; acylamino groups such as acetylamino, propionylamino and mesylamino groups; sulfonamide groups such as ethylsulfonamide and p-toluenesulfonamide groups; ureido groups such as methylureido and phenylureido groups; and amino groups such as diethylamino group.

The aryl groups represented by $R^7$, $R^6$ and $R^9$ in formula (2) include, for example, phenyl and naphthyl groups, which may be optionally substituted. Examples of the substituents in the substituted aryl group include an aryl group such as phenyl and naphthyl; an alkenyl group such as vinyl, allyl and butenyl; an alkynyl group such as ethynyl; a heterocyclic group such as pyridyl, tetrahydropyranyl and sulforanyl; a hydroxy group; an alkoxy group such as methoxy, ethoxy, benzyloxy and polyethyleneoxyalkyl; an alkoxycarbonyl group such as ethoxycarbonyl and benzyloxycarbonyl; a carboxy group; a sulfo group; a halogen atom such as chlorine and bromine; a cyano group; an aryloxy group such as phenoxy and p-tolyloxy; an acyloxy group such as acetyloxy and propionyloxy; an acyl group such as acetyl, propionyl, benzoyl and mesyl; a carbamoyl group such as carbamoyl, N,N-dimethylcarbamoyl, morphorinocarbonyl and piperidinocarbonyl; a sulfamoyl group such as sulfamoyl, N,N-dimethylsulfamoyl, morphorinosulfonyl and piperidinosulfonyl; an acylamino group such as acetylamino, propionylamino and mesylamino; a sulfonamide group such as ethylsulfonamide and p-toluensulfonamide; an ureido group such as methylureido and phenylureido; an amino group such as diethylamino.

The heterocyclic groups represented by $R^7$, $R^8$ and $R^9$ in formula (2) include, for example, piperidyl group, morpholinyl group, furyl group, thienyl group, tetrahydropyranyl group and pyridyl group, which may be optionally substituted. Examples of the substituents in the substituted heterocyclic group include an aryl group such as phenyl and naphthyl; an alkenyl group such as vinyl, allyl and butenyl; a alkynyl group such as ethynyl; an heterocyclic group such as pyridyl, tetrahydropyranyl and sulforanyl; a hydroxy group; an alkoxy group such as methoxy, ethoxy, benzyloxy and polyethyleneoxyalkyl; an alkoxycarbonyl group such as ethoxycarbonyl and benzyloxycarbonyl; a carboxy group; a sulfo group; a halogen atom such as chlorine and bromine; a cyano group; an aryloxy group such as phenoxy and p-tolyloxy; an acyloxy group such as acetyloxy and propionyloxy; an acyl group such as acetyl, propionyl, benzoyl and mesyl; a carbamoyl group such as carbamoyl, N,N-dimethylcarbamoyl, morphorinocarbonyl and piperidinocarbonyl; a sulfamoyl group such as sulfamoyl, N,N-dimethylsulfamoyl, morphorinosulfonyl and piperidinosulfonyl; an acylamino group such as acetylamino, propionylamino and mesylamino; a sulfonamide group such as ethylsulfonamide and p-toluenesulfonamide; an ureido group such as methylureido and phenylureido; an amino group such as diethylamino.

Alternatively, $R^7$ and $R^8$ in formula (2), together with nitrogen atom to which they are attached, may form a heterocyclic ring. Examples of such heterocyclic rings include a 5- to 7-membered N-hetero cyclic, pyrrolidine, piperidine and perhydroazepin rings. These N-heterocyclic rings may optionally contain other hetero atoms such as N, O, and S, thus forming a saturated heterocyclic ring containing two hereto atoms such as imidazolidine, piperazine and morpholine rings.

The divalent linkage groups represented by L in formula (2) include an alkylene group of 1–10 carbon atoms such as methylene, ethylene, propylene and butylene groups, which may be optionally substituted. Examples of the substituents in the substituted alkylene group include aryl group, alkoxy group, hydroxyl group and halogen atom.

In formula (2), E represents a divalent group such as —N(COR$^{11}$)—, —N(CONR$^{12}$R$^{13}$)—, —NR$^{14}$COCONR$^{15}$—, —N(COCONR$^{16}$R$^{17}$)—, —N(SO$_2$R$^{18}$)— or —N(COOR$^{19}$)—, where R$^{11}$–R$^{19}$ independently represent a hydrogen atom, an alkyl group, an aryl group or a heterocyclic group; and R$^{12}$ and R$^{13}$ or R$^{16}$ and R$^{17}$ together with nitrogen atom to which they are attached, may form a ring, with the proviso that only the case where E represents either —NR$^{14}$COCONR$^{15}$— or —N(COCONR$^{16}$R$^{17}$)—, R$^9$ is either a hydrogen atom or an alkyl group. When $R^{11}$–$R^{19}$ independently represent an alkyl group, the alkyl groups are the same as those mentioned for $R^7$, $R^8$ and $R^9$. When $R^{11}$–$R^{19}$ independently represent an aryl group, the aryl groups are identical with those mentioned for $R^7$, $R^8$ and $R^9$. When $R^{11}$–$R^{19}$ independently represent a heterocyclic group, the heterocyclic groups are identical with those mentioned for $R^7$, $R^8$ and $R^9$.

Illustrative examples of the compounds represented by formula (2) are given below, but not limiting thereto.

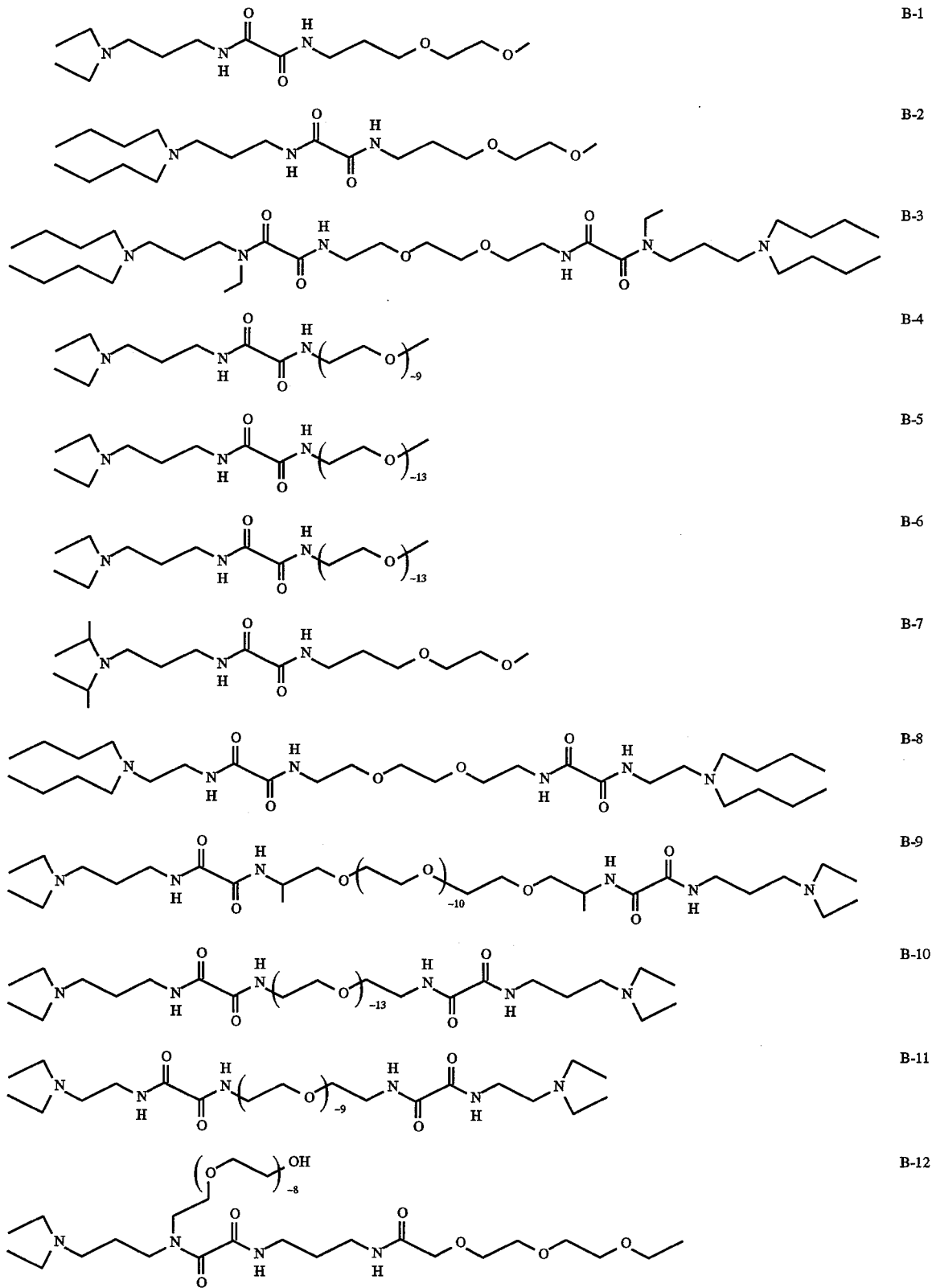

-continued
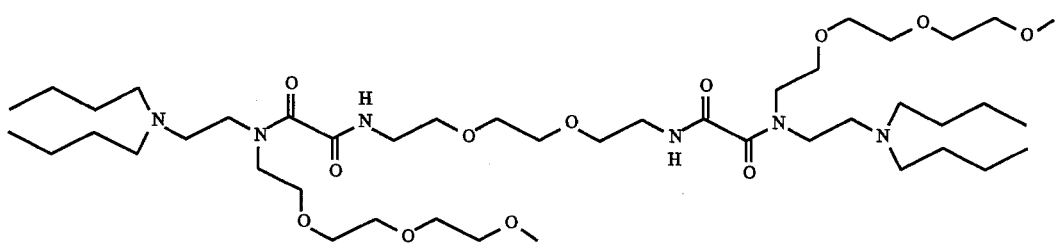
B-13
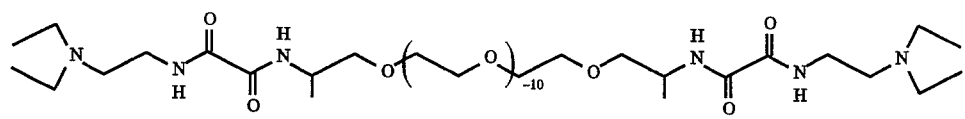
B-14
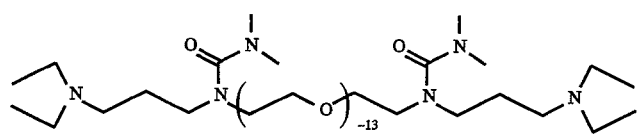
B-15
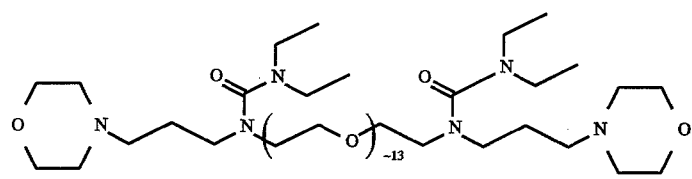
B-16
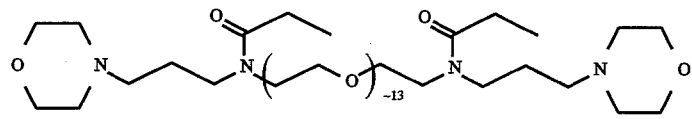
B-17
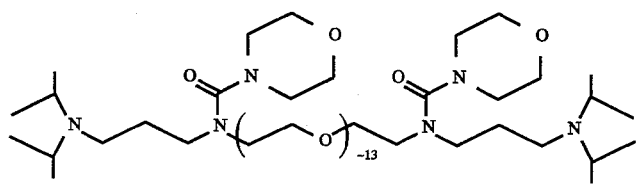
B-18
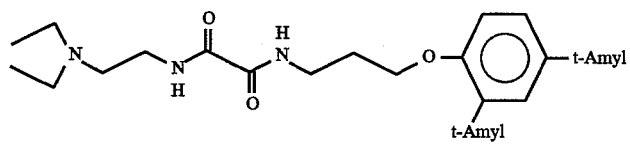
B-19
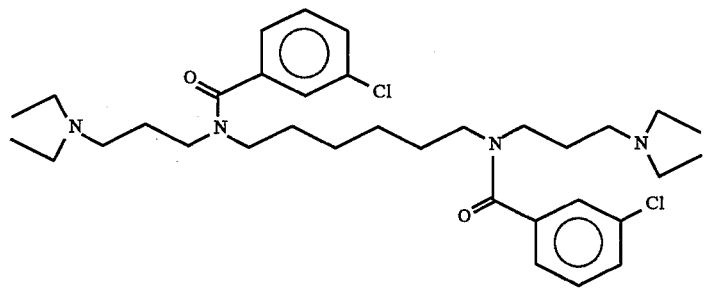
B-20
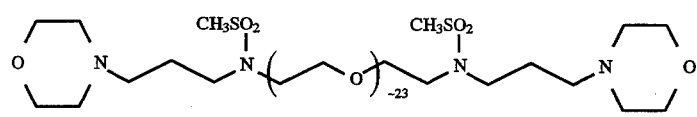
B-21

-continued
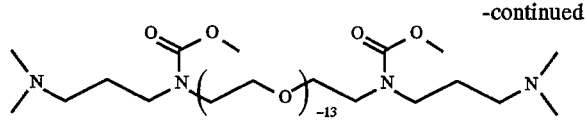  B-22
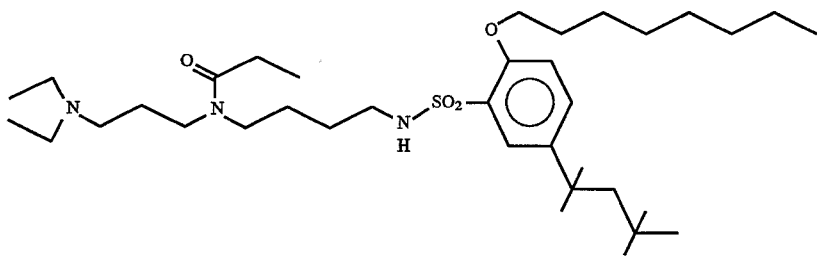  B-23
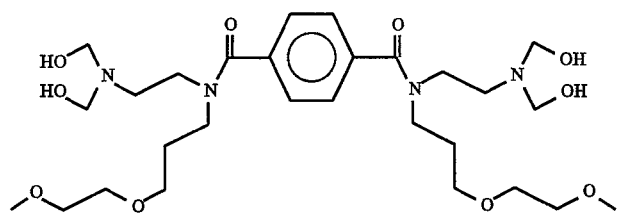  B-24
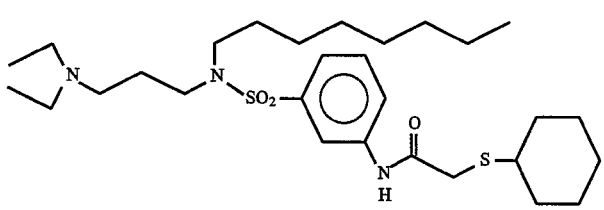  B-25
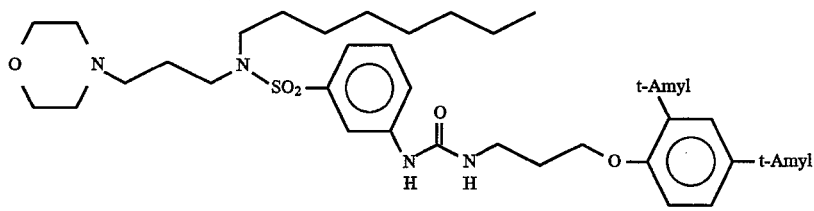  B-26
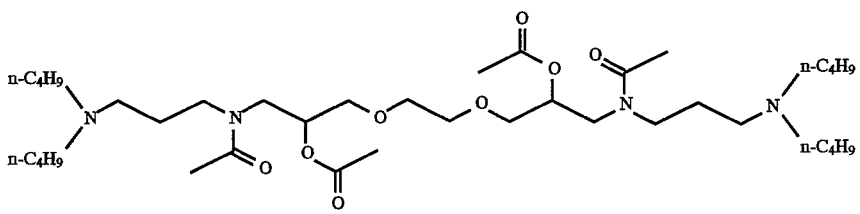  B-27
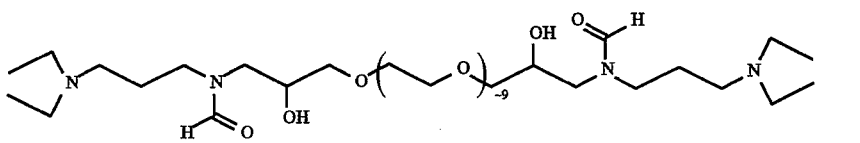  B-28
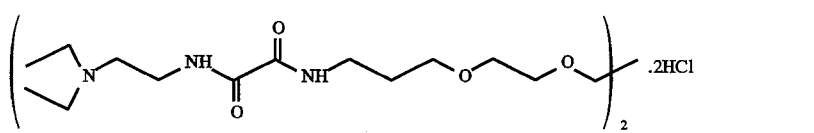  B-29
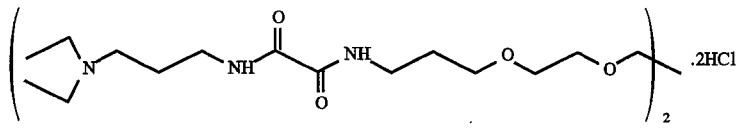  B-30

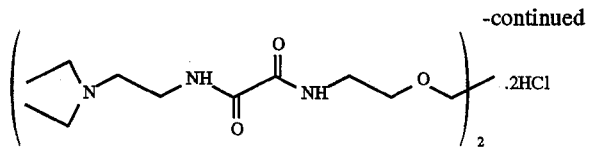

B-31

The synthesis of the contrast promoters represented by formula (1) is illustrated by the following examples.

Synthetic Example 1

Synthesis of Compound A-1

1) Synthesis of intermediate (N,N,N',N'-tetramethylchloroformamidinium chloride)

49.4 g of tetramethylurea were dissolved in 400 ml of 1,2-dichloroethane and 30.0 g of oxalyl chloride were added dropwise to the solution at room temperature over a period of 15 minutes. The resulting solution was stirred at room temperature for 15 minutes and further stirred in an oil bath at 65° C. for 2 hrs. The reaction mixture was concentrated under reduced pressure to 200 ml and allowed to cool, upon which crystals separated out. The crystals were obtained by filtration, washed with ether and dried under reduced pressure to obtain 30.0 g of a white, hygroscopic intermediate.

2) Synthesis of Compound A-1

9.76 g of N,N,N',N'-tetramethylchloroformamidinium chloride were dissolved in 100 ml of methylene chloride and to the solution, 11.14 g of 3-dibutylaminopropylamine were added dropwise under ice-water cooling while stirring. The resulting solution was stirred at room temperature for one hour, washed with an aqueous solution of sodium carbonate and then with water. The organic layer was dried over anhydrous sodium sulfate and concentrated. Removal of excess amine under reduced pressure gave 7.5 g of Compound A-1 as a light brown, viscous, oily product.

Synthetic Example 2

Synthesis of Compound A-29

10 g of 2-diisopropylaminoethylchloride hydrochloride were dissolved in 30 ml of methanol, to the solution was added 9.1 ml of 5.5M methanol solution of sodium methylate and then 7.5 ml (0.06 mol) of tetramethylguanidine and the mixture was heated under reflux for 8 hrs. The precipitate by sodium chloride was filtered off and the filtrate was concentrated under reduced pressure at 90° C. to remove all volatile components. To the concentrate was added 20 ml of methanol, the solution was filtered, butylmethylether was added for precipitation. Purification of the reaction product by twice repeated similar procedure gave 6 g of deliquescent, Compound A-29 as white crystals.

Other exemplified Compounds A-2 to A-28 and A-30 to A-32 could be readily synthesized by a similar method as mentioned above.

Synthetic Example 3

Synthesis of Compound B-1

13.0 g of N,N-diethyl-1,3-diaminopropane were added to 70 ml of diethyl oxalate with stirring at room temperature over a period of 20 minutes. After stirring at room temperature for 2 hours, excess diethyl oxalate was distilled off under reduced pressure to obtain 21.7 g of N,N-diethyl-N'-ethoxalyl-1,3-diaminopropane as an oily product. 6.90 g of this oily product and 3.99 g of 3-(2-methoxyethoxy)propylamine were dissolved in 30 ml of methanol and the solution was heated under reflux for 1 hour. The solvent was distilled off under reduced pressure to obtain 9.51 g of Compound B-1 as an oily product.

Synthetic Example 4

Synthesis of Compound B-9

30.0 g of O,O'-bis(2-aminopropyl)polyethylene glycol 500 was added dropwise to 80 ml of diethyl oxalate with stirring at room temperature over a period of 60 minutes. After stirring for 4 hours at room temperature, excess diethyl oxalate was distilled off under reduced pressure to obtain 35.5 g of O,O'-bis(2-ethoxyoxalylamino-propyl) polyethylene glycol as an oily product. 28.0 g of this oily product and 13.0 g of N,N-diethyl-1,3-diaminopropane were dissolved in 150 ml of methanol and the solution was heated under reflux for one hour. Distilling off the solvent under reduced pressure and isolation by silica gel column chromatography gave 34.5 g of Compound B-9 as an oily product.

Synthetic Example 5

Synthesis of Compound B-27

10.1 g of ethylene glycol diglycidyl ether and 5 27.1 g of N,N-dibutyl-1,3-diaminopropane were dissolved in 70 ml of ethanol and the solution was stirred at 60° C. for 3 hrs. Removal of the solvent and excess amine by distilling off under reduced pressure and isolation by silica gel column chromatography gave 23.5 g of an oily intermediate. To 21.8 g of the intermediate were added 140 ml of methylene chloride and then 20.4 g of acetic anhydride with stirring in ice water over a period of 10 minutes. After stirring for 6 hours at room temperature, 200 ml of 10% $NaHCO_3$ were added and the resulting solution was extracted with methylene chloride. The methylene chloride layer was washed with water, dried and distilled off under reduced pressure to obtain 24.2 g of Compound B-27 as an oily product.

Synthetic Example 6

Synthesis of Compound B-29

11.6 g of diethylaminoethylamine were dissolved in 20 ml of methylene chloride and the solution was added dropwise at −10° C. to a solution of 12.5 g (0.1 mol) of methoxyoxalyl chloride in 30 ml of methylene chloride. The mixture was stirred for one hour and heated to room temperature. Methylene chloride was evaporated in vacuum, the residue was dissolved in methanol and 11 g (0.05 mol) of 1,13-diamino-4,7,10-trioxatridecane were added. The mixture was stirred at 60° C. for 8 hrs and methanol was distilled off under reduced pressure. The oily residue was washed with ether and dried in vacuum.

Other exemplified Compounds B-2 to B-8, B-10 to B-26, B-28 and B-30 to B-31 could be readily synthesized by a similar method as mentioned above.

The compounds of formulas (1) and (2) according to the present invention are preferably incorporated in the silver halide emulsion layer when they are incorporated in the photographic photosensitive materials, but they may also be incorporated in other non-photosensitive, hydrophilic colloid layers such as a protective layer, an intermediate layer, a filter layer and an antihalation layer. Specifically, when the compound used is water-soluble, it may be added in the form of an aqueous solution to a hydrophilic colloid solution. When the compound used is slightly soluble in water, it is added to a hydrophilic colloid solution in the form of a solution in a water-miscible organic solvent such as an alcohol (e.g., methanol, ethanol, propanol or a fluorinated alcohol), a ketone (e.g., acetone or methyl ethyl ketone), dimethylacetamide, dimethyl sulfoxide and methyl cellosolve. When the compound is added to a silver halide emulsion layer, it can be added in any time during preparation of the emulsion, but is preferably added after completion of chemical ripening and before coating. Especially preferably, it is incorporated in a coating solution prepared for coating. Amount of the compound added is preferably $1.0 \times 10^{-4}$ to $1.0 \times 10^{-1}$ mol, more preferably $5.0 \times 10^{-4}$ to $5.0 \times 10^{-2}$ mol per mol of silver halide. When the compound is incorporated in the developer, $5 \times 10^{-3}$ to 0.30 mol per liter of the developer is preferable. The present compounds of formulas (1) and (2) have a high-contrast promoting effect when used in the system where so-called high-contrast silver images are obtained. The compounds of formulas (1) and (2) exhibit remarkable effect in the system where a hydrazine derivative is used as a nucleating agent.

The hydrazine derivatives used in the present invention include the compounds represented by the following formula (3).

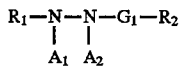

wherein $A_1$ and $A_2$ both represent a hydrogen atom or one of them represents a hydrogen atom and the other represents a sulfonyl group or an acyl group, $R_1$ represents an aliphatic group, an aromatic group or a heterocyclic group, $G_1$ represents a carbonyl group, a sulfonyl group, a sulfoxy group, phosphoryl group, oxalyl group or an iminomethylene group, and $R_2$ represents a hydrogen atom, an aliphatic group, an aromatic group, an alkoxy group, an aryloxy group, an amino group or a group represented by formula (4):

wherein $Q^+$ represents a group containing a cationic group and $A^-$ represents an anion, but A is unnecessary when $Q^+$ contains a sulfo group.

The formulas (3) and (4) will be explained in detail. In formula (3), as $A_1$ and $A_2$ include hydrogen atom, alkylsulfonyl and arylsulfonyl groups of 20 or less carbon atoms (preferably a phenylsulfonyl group or a phenylsulfonyl group substituted so that it has a sum of Hammett's value $\sigma_p$ of −0.5 or more), an acyl group of 20 or less carbon atoms (preferably a benzoyl group or a benzoyl group substituted so that it has a sum of Hammett's value $\sigma_p$ of −0.5 or more) or substituted or unsubstituted and straight chain, branched chain or cyclic aliphatic acyl group (the substitutents include, for example, halogen atom, ether group, sulfonamide group, amide group, hydroxy group, carboxyl group and sulfo group) and $A_1$ and $A_2$ are most preferably hydrogen atom. The aliphatic group represented by $R_1$ includes a straight chain, branched chain or cyclic alkyl, alkenyl or alkynyl group. The aromatic group represented by $R_1$ includes monocyclic or bicyclic aryl groups such as phenyl group and naphthyl group. The heterocyclic group represented by $R_1$ includes 3-to 10-membered saturated or unsaturated heterocyclic rings containing at least one of N, O and S atoms, and these may be monocyclic or may form condensed rings with other aromatic or heterocyclic rings. The heterocyclic rings are preferably 5- or 6-membered aromatic heterocyclic groups, examples of which include those which contain pyridyl group, imidazolyl group, quinolinyl group, benzimidazolyl group, pyrimidyl group, pyrazolyl group, isoquinolinyl group, thiazolyl group and benzothiazolyl group. $R_1$ may be substituted with a substituent. Examples of the substituent include alkyl group, aralkyl group, alkoxy group, aryl group, substituted amino group, acylamino group, sulfonylamino group, ureido group, urethane group, aryloxy group, sulfamoyl group, carbamoyl group, alkylthio group, arylthio group, sulfonyl group, sulfinyl group, hydroxyl group, halogen atom, cyano group, sulfo group, carboxyl group, ammonium group, pyridinium group, thiuronium and isothioureido group. These groups may link to each other to form a ring when this is possible. $R_1$ is preferably an aromatic group, more preferably an aryl group. Furthermore, $R_1$ may be a ballast-containing one normally used in inert photographic additives such as coupler. The ballast is a group having 8 or more carbon atoms and relatively inert to photographic processing and can be selected, for example, from alkyl group, alkoxy group, phenyl group, alkylphenyl group, phenoxy group, alkylphenoxy group, etc. $Q^+$ in formula (4) is a group containing a cationic group having at least one quaternary nitrogen atom and bonds to $G_1$ through a straight or branched chain hydrocarbon chain having 1–4 carbon atoms and a part or the whole of this chain may constitute a part of a heterocyclic ring having a quaternary nitrogen atom. Preferable examples of $Q^+$ are trialkylammoniumalkyl group, pyridinium-1-ylalkyl group, 1-alkylpyridinium-2-yl group, 1-alkylpyridinium-3-yl group, 1-alkylpyridinium-4-yl group, thiazolinium-3-ylalkyl group, oxazolinium-3-ylalkyl group and 1-alkylimidazolium-3-ylalkyl group. These groups may be substituted and as the substituents preferred are those which are referred to above as the substituents for $R^1$. Furthermore, when these groups form a ring structure, the ring may condense with other rings. $A^-$ is a counter anion for $Q^+$ and preferred are $Cl^-$, $Br^-$, a p-toluenesulfonate and a methylsulfonate. $A^-$ is not present when the substituent in $Q^+$ is sulfo group and an inner salt is formed.

$G_1$ represents a carbonyl group, a sulfonyl group, a sulfoxy group, a phosphoryl group, an oxalyl group or an iminomethylene group and preferred are carbonyl group and oxalyl group. The aliphatic group represented by $R_2$ is preferably an alkyl group of 1–5 carbon atoms and the aromatic group represented by $R_2$ is preferably a monocyclic or bicyclic aryl group (such as one containing a benzene ring). In the case of $G_1$ being a carbonyl group, preferred as $R_2$ are hydrogen atom, alkyl groups (such as methyl group, trifluoromethyl group, 3-hydroxypropyl group, 3-methanesulfonamidopropyl group, and phenylsulfonylmethyl group), aralkyl groups (such as 2-hydroxybenzyl group), aryl groups (such as phenyl group, 3,5-dichlorophenyl group, 2-methanesulfonamidophenyl group, 4-methanesulfonamidephenyl group and 2-hydroxymethylphenyl group) and groups represented by formula (4). Especially preferred are hydrogen atom and the groups represented by formula (4). $R_2$ may be substituted and the substituents may be those which are enumerated hereabove for $R_1$. In the case of $G_1$ being an oxalyl group, preferred as $R_2$ are alkoxy groups (such as methoxy group, ethoxy group, isopropoxy group and methoxyethoxy group), aryloxy groups (such as phenoxy group, 2-hydroxymethylphenoxy group and 4-chlorophenoxy group), amino groups (such as 3-hydroxypropylamino group, 2,3-dihydroxypropylamino group, 2-dimethylaminoethylamino group and 3-diethylaminopropylamino group) and groups represented by formula (4). Amino groups are especially preferred. $R_1$ and $R_2$ may be those which contain a group capable of enhancing the adsorption of the compound onto the surface of the silver halide grains. Such adsorption group includes, for example, thiourea group, heterocyclic thioamide group, mercapto heterocyclic group and triazole group described in U.S. Pat. No. 4,355,105. Furthermore, $R_2$ may be those which induce a cyclization reaction capable of splitting the site of $G_1$—$R_2$ from the other molecule to produce a cyclic structure containing the atoms of the site of —$G_1$—$R_2$. Examples are those which are described in Japanese Patent Kokai No. 63-29751.

Nonlimiting examples of the compounds represented by formula (3) are shown below.

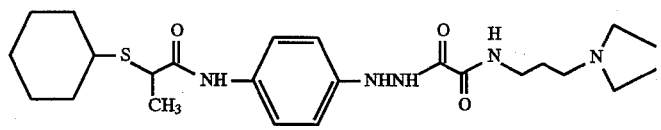

H-1

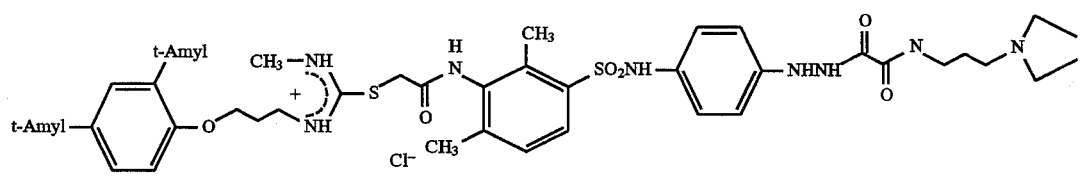

H-2

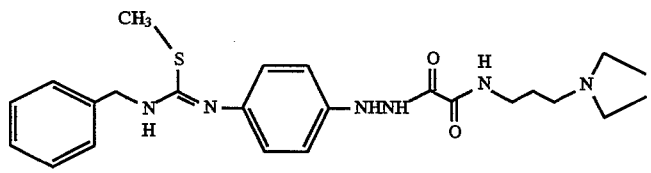

H-3

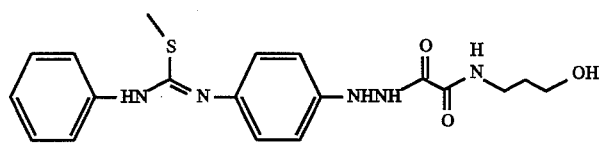

H-4

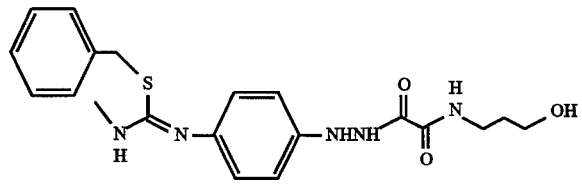

H-5

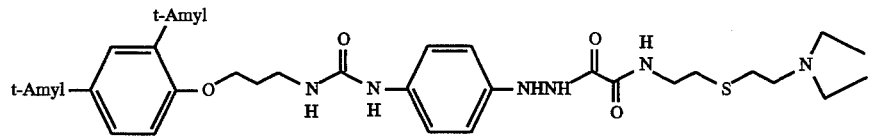

H-6

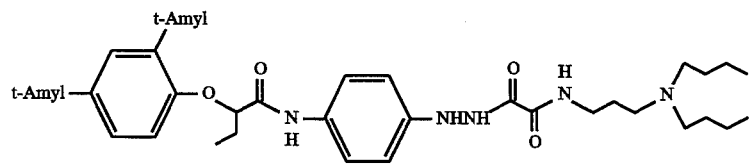

H-7

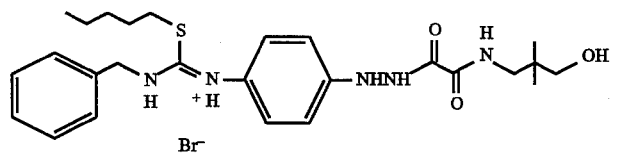

H-8

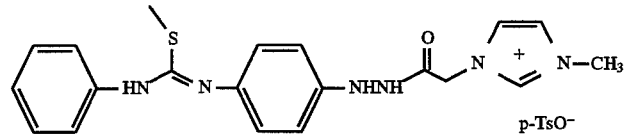

H-9

-continued
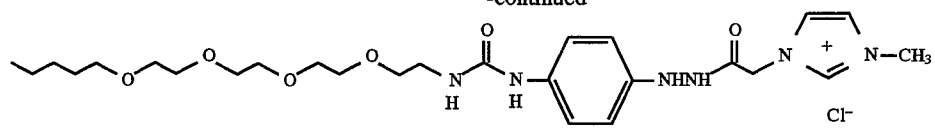
H-10
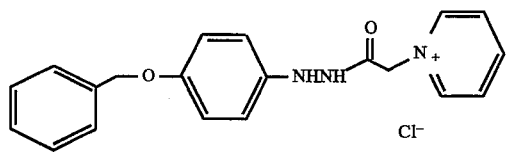
H-11
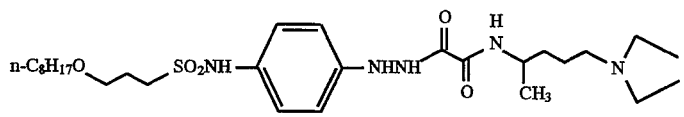
H-12
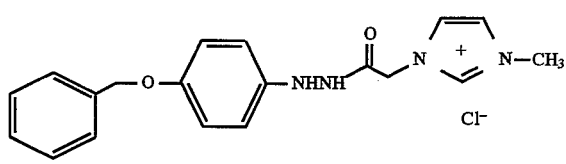
H-13
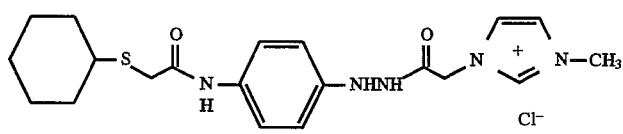
H-14
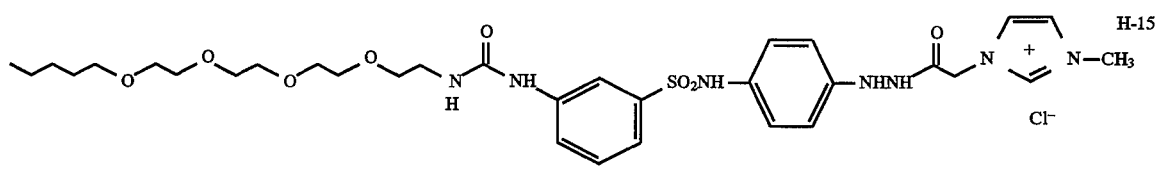
H-15
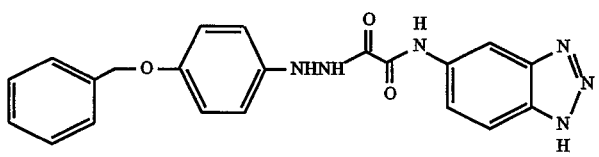
H-16
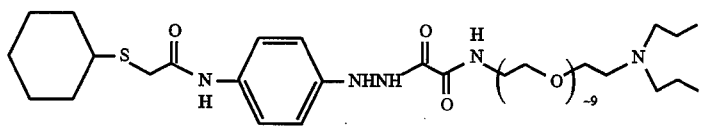
H-17
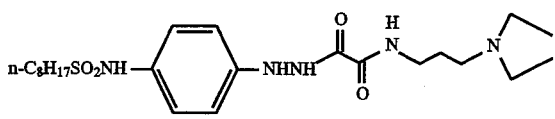
H-18
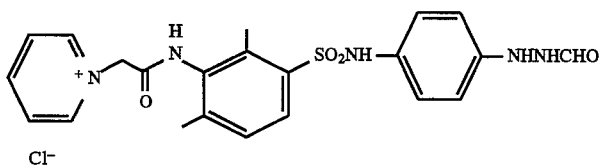
H-19
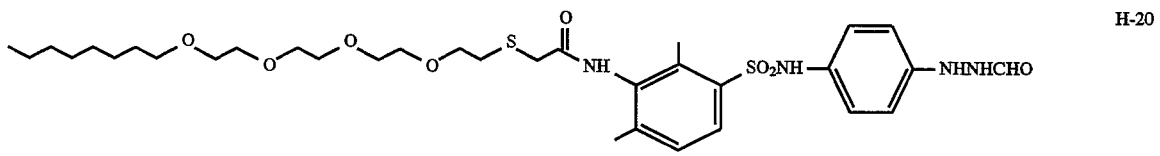
H-20

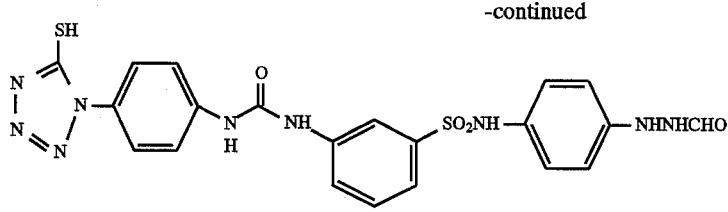

H-21

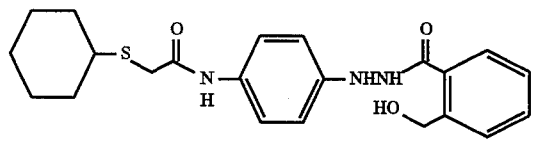

H-22

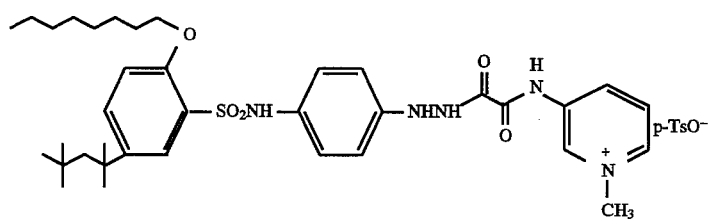

H-23

The hydrazine compounds of the present invention can be synthesized by the processes described, for example, in Japanese Patent Kokai Nos. 61-213847, 62-178246, 62-180361, 62-260153 and 63-253357, U.S. Pat. Nos. 4,684,604, 3,279,529, 4,377,634, 4,332,878 and 4,937,160, and Japanese Patent Application No. 63-98803.

The hydrazine compounds of the present invention can be used as solutions in water-miscible organic solvents, for example, alcohols (such as methanol, ethanol, propanol and fluorinated alcohols), ketones (such as acetone and methyl ethyl ketone), dimethylformamide, dimethylacetamide, dimethyl sulfoxide and methyl cellosolve. Furthermore, they may be used as emulsified dispersions prepared by dissolving them using oils such as dimethyl phthalate, tricresyl phosphate, glyceryl triacetate and diethyl phthalate or co-solvents such as ethyl acetate and cyclohexanone and mechanically emulsifying them by the well known emulsification dispersing method. Alternatively, powders of the hydrazine compounds are dispersed in water by ball mill or colloid mill or by ultrasonics by a method known as the solid dispersing method.

The silver halides used for the photosensitive silver halide emulsion in the photosensitive materials of the present invention are not limitative, but preferred are surface latent image type silver halide emulsions. As the silver halides, there may be used silver chloride, silver chlorobromide, silver chloroiodobromide, silver iodobromide, silver bromide and the like. When silver chloroiodobromide or silver iodobromide is used, content of silver iodide is preferably 5 mol % or less. Form, habit and size distribution of the silver halide grains are not critical, but those of 0.7μ or smaller in grain size are preferred. Sensitivity of the silver halide emulsion can be increased with gold compounds such as chloroaurates and gold trichloride, salts of noble metals such as rhodium and iridium, sulfur compounds capable of reacting with silver salts to form silver sulfides, and reducing materials such as stannous salts and amines without causing increase in grain size. Moreover, salts of noble metals such as rhodium and iridium or iron compounds such as potassium ferricyanide can be allowed to be present during physical ripening or nucleation of silver halide grains. Especially, addition of rhodium salts or complex salts thereof is preferred since they further promote the effect of the present invention of attaining the super-contrast photographic characteristics in a short time.

In the present invention, the surface latent image type silver halide emulsion means an emulsion comprising silver halide grains higher in surface sensitivity than in internal sensitivity and this emulsion preferably has the difference between the surface sensitivity and the internal sensitivity as specified in U.S. Pat. No. 4,224,401. The silver halide emulsion is preferably monodispersed and especially desirably has the monodispersibility specified in the above U.S. Pat. No. 4,224,401. The silver halide emulsion used in the present invention more preferably contains a water-soluble rhodium salt (for example, rhodium dichloride, rhodium trichloride, potassium hexachlororhodate (III) and ammonium hexachlororhodate (III)). The rhodium salts are added preferably before completion of the first ripening in preparation of the emulsion. Amount of the rhodium salt is preferably $1\times10^{-7}$ to $1\times10^{-4}$ mol for 1 mol of silver halide. The average grain size of the silver halide used in the present invention is preferably 0.7 μm or smaller, especially preferably 0.1–0.4 μm. The silver halide grains may be in a regular form such as, for example, a cube or an octahedron or in the form of a mixed crystal and are preferably in the form of so-called monodispersed emulsion which is relatively narrow in the grain size distribution. The monodispersed emulsion here means an emulsion wherein 90% or more, preferably 95% or more of total grains have a grain size with ±40% of the average grain size. For reaction of a soluble silver salt with a soluble halogen salt for preparation of silver halide emulsions in the present invention, any means of the single jet method, the double jet method, the reverse mixing method in which the emulsion is prepared in the presence of excess of silver ion, and others can be employed. For the purpose of the present invention, the double jet method is especially preferred which comprises simultaneously adding the soluble salt and the soluble halogen salt in the presence of an acidic solution to prepare the grains. The silver halide emulsion prepared in this way may be or may not be chemically sensitized. It is rather preferred for the use as so-called roomlight photosensitive materials handled in safelight environment which can be called substantially a light room that the emulsion is not chemically sensitized from the viewpoint of improvement of handleability. If the chemical sensitization is effected, the usual sulfur sensitization, selenium sensitization, tellurium sensitization, reduction sensitization, etc. are employed.

The hydrazine compound is preferably contained in the silver halide emulsion layer, but may be contained in a hydrophilic colloid layer contiguous to the surface latent image type silver halide emulsion layer. Such hydrophilic colloid layer may be any layers having various functions as far as they do not hinder the diffusion of the hydrazine compound into the silver halide grains, examples of which include undercoat layer, intermediate layer, filter layer, protective layer and antihalation layer. The content of the hydrazine compound in the layer can widely vary depending on the characteristics of silver halide emulsions used, the chemical structure of the hydrazine compound and the developing conditions, but a range of about $1 \times 10^{-6}$ to $1 \times 10^{-1}$ mol per mol of silver in the surface latent image type silver halide emulsion is practically useful.

The photographic emulsion used in the present invention may be spectrally sensitized with methine dyes and the like. The dyes used include cyanine dyes, merocyanine dyes, composite cyanine dyes, composite merocyanine dyes, holopolar cyanine dyes, hemicyanine dyes, styryl dyes and hemioxonol dyes. Especially useful dyes are those which belong to cyanine dyes, merocyanine dyes and composite merocyanine dyes. These sensitizing dyes may be used each alone or in combination. The sensitizing dyes are often used in combination especially for the purpose of supersensitization. The emulsion may contain together with the sensitizing dye a dye which per se has no spectral sensitizing action or a substance which absorbs substantially no visible light and shows supersensitizing action.

Gelatin can be advantageously used as binders or protective colloids usable in the emulsion layer and the intermediate layer of the photosensitive materials of the present invention, but other hydrophilic colloids may also be used. For example, there may be used various synthetic hydrophilic polymer materials, e.g., one of or copolymers of proteins such as gelatin derivatives, graft polymers of gelatin with other polymers, albumin and casein; cellulose derivatives such as hydroxyethylcellulose, carboxymethylcellulose and cellulose sulfate esters; sugar derivatives such as sodium alginate and starch derivatives; polyvinyl alcohol; partial acetals of polyvinyl alcohol; poly-N-vinylpyrrolidone; polyacrylic acid; polymethacrylic acid; polyacrylamide; and polyvinylimidazole. As the gelatin, there may be used lime-treated gelatins and furthermore, acid-treated gelatins and enzyme-treated gelatins described in Bull. Soc. Sci. Phot. Japan, No.16, page 30 (1966). Moreover, hydrolyzates and enzyme-decomposition products of gelatins may also be used.

Conventional safelight dyes may be added to the emulsion layer or other hydrophilic colloid layers in order that the materials can be handled under roomlight in producing super-high contrast images using hydrazine compounds. Various compounds can be contained in the photographic emulsion used in the present invention in order to inhibit fog which may occur during preparation, storing or photographic processing of the photosensitive materials or in order to stabilize photographic performances. That is, there may be used various compounds known as antifoggants or stabilizers, for example, azoles such as benzothiazolium salts, nitroimidazoles, nitrobenzimidazoles, chlorobenzimidazoles, mercaptothiazoles, mercaptobenzothiazoles, mercaptothiadiazoles, aminotriazoles, benzotriazoles and mercaptotetrazoles; mercaptopyrimidines, mercaptotriazines, thioketo compounds, azaindenes, etc. Among them, especially preferred are benzotriazoles (such as 5-methylbenzotriazoles) and nitroindazoles (such as 5-nitroindazole). These compounds may also be contained in processing solutions.

In the photographic photosensitive materials of the present invention, the photographic emulsion layer and other hydrophilic colloid layers may contain inorganic or organic hardeners. For example, there may be used chromium salts (such as chrome alum), aldehydes (such as formaldehyde and glyoxal), N-methylol compounds, dioxane derivatives (such as 2,3-dihydroxydioxane), active vinyl compounds, active halogen compounds (such as 2,4-dichloro-6-hydroxy-S-triazine), etc. These are used each alone or in combination. Furthermore, the photosensitive silver halide emulsion layer or the layers contiguous thereto may contain the compounds described in Research Disclosure, No. 17465, XXI, B-D for increase of sensitivity, increase of contrast and acceleration of development- Polyethylene glycol and derivatives thereof are especially preferred. The photographic emulsion layer or other hydrophilic colloid layers of the photosensitive materials made using the present invention may contain surface active agents for various purposes such as coating aid, antistatic effect, improvement of slipperiness, emulsification dispersing, inhibition of adhesion and improvement of photographic characteristics (such as acceleration of development, increase of contrast and sensitization). For example, there may be used nonionic surface active agents such as saponin (e.g., steroid type), alkylene oxide derivatives (e.g., polyethylene glycol and polyethylene glycol alkyl ethers), glycidol derivatives (e.g., polyglycerides of alkenylsuccinic acids), fatty acid esters of polyhydric alcohols and alkyl esters of sugars, anionic surface active agents containing acid groups, e.g., carboxyl group, sulfo group, phospho group, sulfate ester group and phosphate ester group, such as alkylcarboxylate salts, alkylsulfate esters and alkylphosphate esters, amphoteric surface active agents such as amino acids, aminoalkylsufonic acids, aminoalkylsulfate esters and aminoalkylphosphate esters, and cationic surface active agents such as aliphatic or aromatic quaternary ammonium salts and heterocyclic quaternary ammonium salts, e.g., pyridinium and imidazolium.

The photographic emulsion layer or other hydrophilic colloid layers of the photosensitive materials used in the present invention may contain decomposition products of water-insoluble or hardly soluble synthetic polymers for improving dimensional stability. Examples are polymers containing, as monomer component, one or combination of alkyl (meth)acrylates, alkoxyalkyl (meth)acrylates, glycidyl (meth)acrylates, (meth)acrylamides, vinyl acetate, acrylonitrile, olefins, styrene, etc. or combination of them with acrylic acid, methacrylic acid, $\alpha,\beta$-unsaturated dicarboxylic acids, hydroxyalkyl (meth)acrylates, styrenesulfonic acid, etc.

For obtaining super-high contrast photographic characteristics using the silver halide photographic photosensitive materials of the present invention, it is not necessary to use the conventional lith developers or the high alkali developers having a pH of near 13 described in U.S. Pat. No. 2,419,975, but stable developers can be used. That is, developers containing sulfite ions in a sufficient amount (especially, 0.15 mol/l or higher) as a preservative can be used for the silver halide photographic photosensitive materials of the present invention and furthermore, negative images of sufficiently super-high contrast can be obtained with developers having a pH of 9.5 or higher, especially 10–11.0.

The present invention is further illustrated by the following nonlimiting examples.

Example 1

1 g/l mol Ag (1 g per mol of Ag) of 6-methyl-4-hydroxy-1,3,3a,7-tetrazaindene was incorporated in a monodispersed silver chlorobromide emulsion having an average grain size of 0.25 μm and containing iridium which was prepared by the controlled double jet method. To the emulsion were added 300 mg/l mol Ag(300 mg per mol of Ag) of anhydro-5,5'-dichloro-9-ethyl-3,3'-di-(3-sulfopropyl) oxacarbocyanine hydroxide pyridinium as a sensitizing dye, the hydrazine compounds and the contrast promoters as shown in Table 1. To the thus obtained emulsion were added 2 g/m² of a dispersion of polyethylene acrylate and 2.5 g/m² of gelatin and the emulsion was coated on a polyethylene terephthalate film at a coating amount of 3.5 g/m² in terms of silver. For preparing comparative samples on the contrast promoter, the following comparative compounds (1), (2) and (3) were used in the same manner as above.

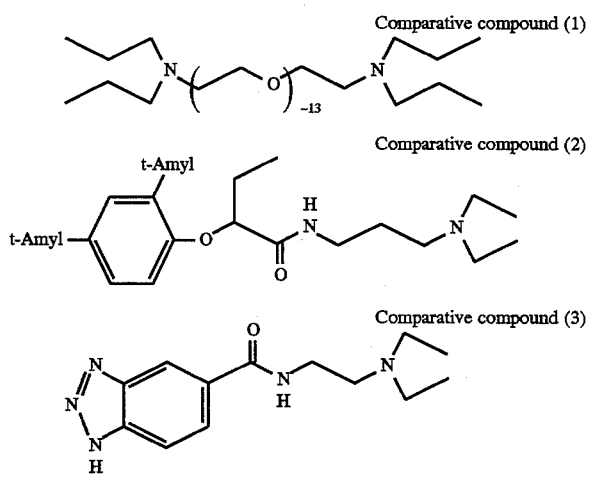

The resulting samples were exposed through an optical wedge using a printer having a tungsten lamp light source, then developed with a developer having the following composition for 20 seconds at 38° C., stopped, fixed, washed with water and dried. Relative photographic sensitivity, contrast and dot quality of the samples were evaluated. The contrast was expressed by inclination of the linear part of characteristic curve (tanθ of optical density of 0.1–2.5). The dot quality is a subjective measure and is ranked in five grades with 1 being very poor and 5 being very good. The dot quality of 3 and higher grades is practically usable. The results are shown in Tables 3 and 4.

Developer (concentrated)

| | |
|---|---|
| Hydroquinone | 65 g |
| 4-Hydroxymethyl-4-methyl-1-phenyl-3-pyrazolidone | 2.9 g |
| Sodium pyrosulfite | 145 g |
| Pentasodium diethylenetriaminepentaacetate | 6.0 g |
| Boric acid | 6.9 g |
| Sodium bromide | 12 g |
| 1-Phenyl-5-mercaptotetrazole | 0.05 g |
| Sodium hydroxide | 23 g |
| Benzotriazole | 0.4 g |
| Potassium hydroxide | 80 g |
| Potassium carbonate | 80 g |
| Diethylene glycol | 120 g |
| Water to make up 1 liter in total | |

The above concentrated developer was diluted with water in an amount 4 parts based on 1 part of the developer to prepare a developer having a pH of 10.5.

TABLE 1

| Sample No. | Hydrazine compound Kind | Amount (mol/mol Ag) | Promoter Kind | Amount (g/m²) | Note |
|---|---|---|---|---|---|
| 1 | H-1 | $7 \times 10^{-4}$ | None | — | Comparative |
| 2 | H-1 | $7 \times 10^{-4}$ | Comparative compound (1) | $1 \times 10^{-2}$ | Comparative |
| 3 | H-1 | $7 \times 10^{-4}$ | Comparative compound (1) | $2 \times 10^{-2}$ | Comparative |
| 4 | H-1 | $7 \times 10^{-4}$ | Comparative compound (2) | $1 \times 10^{-2}$ | Comparative |
| 5 | H-1 | $7 \times 10^{-4}$ | Comparative compound (2) | $2 \times 10^{-2}$ | Comparative |
| 6 | H-1 | $7 \times 10^{-4}$ | Comparative compound (3) | $1 \times 10^{-2}$ | Comparative |
| 7 | H-1 | $7 \times 10^{-4}$ | Comparative compound (3) | $2 \times 10^{-2}$ | Comparative |
| 8 | H-1 | $7 \times 10^{-4}$ | A-1 | $1 \times 10^{-2}$ | The present invention |
| 9 | H-1 | $7 \times 10^{-4}$ | A-1 | $2 \times 10^{-2}$ | The present invention |
| 10 | H-1 | $7 \times 10^{-4}$ | A-3 | $1 \times 10^{-2}$ | The present invention |
| 11 | H-1 | $7 \times 10^{-4}$ | A-3 | $2 \times 10^{-2}$ | The present invention |
| 12 | H-1 | $7 \times 10^{-4}$ | A-7 | $1 \times 10^{-2}$ | The present invention |
| 13 | H-1 | $7 \times 10^{-4}$ | A-7 | $2 \times 10^{-2}$ | The present invention |
| 14 | H-3 | $7 \times 10^{-4}$ | Comparative compound (1) | $1 \times 10^{-2}$ | Comparative |
| 15 | H-3 | $7 \times 10^{-4}$ | Comparative compound (1) | $2 \times 10^{-2}$ | Comparative |
| 16 | H-3 | $7 \times 10^{-4}$ | Comparative compound (3) | $1 \times 10^{-2}$ | Comparative |
| 17 | H-3 | $7 \times 10^{-4}$ | Comparative compound (3) | $2 \times 10^{-2}$ | Comparative |
| 18 | H-3 | $7 \times 10^{-4}$ | A-1 | $1 \times 10^{-2}$ | The present invention |
| 19 | H-3 | $7 \times 10^{-4}$ | A-1 | $2 \times 10^{-2}$ | The present invention |
| 20 | H-3 | $7 \times 10^{-4}$ | A-3 | $1 \times 10^{-2}$ | The present invention |
| 21 | H-3 | $7 \times 10^{-4}$ | A-3 | $2 \times 10^{-2}$ | The present invention |
| 22 | H-3 | $7 \times 10^{-4}$ | A-13 | $1 \times 10^{-2}$ | The present invention |
| 23 | H-3 | $7 \times 10^{-4}$ | A-13 | $2 \times 10^{-2}$ | The present invention |

TABLE 2

| Sample No. | Hydrazine compound Kind | Amount (mol/mol Ag) | Promoter Kind | Amount (g/m²) | Note |
|---|---|---|---|---|---|
| 24 | H-12 | $7 \times 10^{-4}$ | None | — | Comparative |
| 25 | H-12 | $7 \times 10^{-4}$ | Comparative compound (1) | $2 \times 10^{-2}$ | Comparative |
| 26 | H-12 | $7 \times 10^{-4}$ | Comparative compound (1) | $4 \times 10^{-2}$ | Comparative |
| 27 | H-12 | $7 \times 10^{-4}$ | Comparative compound (2) | $2 \times 10^{-2}$ | Comparative |
| 28 | H-12 | $7 \times 10^{-4}$ | Comparative compound (2) | $4 \times 10^{-2}$ | Comparative |
| 29 | H-12 | $7 \times 10^{-4}$ | Comparative compound (3) | $2 \times 10^{-2}$ | Comparative |
| 30 | H-12 | $7 \times 10^{-4}$ | Comparative compound (3) | $4 \times 10^{-2}$ | Comparative |
| 31 | H-12 | $7 \times 10^{-4}$ | B-9 | $2 \times 10^{-2}$ | The present invention |
| 32 | H-12 | $7 \times 10^{-4}$ | B-9 | $4 \times 10^{-2}$ | The present invention |
| 33 | H-12 | $7 \times 10^{-4}$ | B-10 | $2 \times 10^{-2}$ | The present invention |
| 34 | H-12 | $7 \times 10^{-4}$ | B-10 | $4 \times 10^{-2}$ | The present invention |
| 35 | H-12 | $7 \times 10^{-4}$ | B-14 | $2 \times 10^{-2}$ | The present invention |
| 36 | H-12 | $7 \times 10^{-4}$ | B-14 | $4 \times 10^{-2}$ | The present invention |
| 37 | H-3 | $7 \times 10^{-4}$ | Comparative compound (1) | $2 \times 10^{-2}$ | Comparative |
| 38 | H-3 | $7 \times 10^{-4}$ | Comparative compound (1) | $4 \times 10^{-2}$ | Comparative |
| 39 | H-3 | $7 \times 10^{-4}$ | Comparative compound (3) | $2 \times 10^{-2}$ | Comparative |
| 40 | H-3 | $7 \times 10^{-4}$ | Comparative compound (3) | $4 \times 10^{-2}$ | Comparative |
| 41 | H-3 | $7 \times 10^{-4}$ | B-14 | $2 \times 10^{-2}$ | The present invention |
| 42 | H-3 | $7 \times 10^{-4}$ | B-14 | $4 \times 10^{-2}$ | The present invention |
| 43 | H-3 | $7 \times 10^{-4}$ | B-16 | $2 \times 10^{-2}$ | The present invention |
| 44 | H-3 | $7 \times 10^{-4}$ | B-16 | $4 \times 10^{-2}$ | The present invention |
| 45 | H-3 | $7 \times 10^{-4}$ | B-17 | $2 \times 10^{-2}$ | The present invention |
| 46 | H-3 | $7 \times 10^{-4}$ | B-17 | $4 \times 10^{-2}$ | The present invention |

TABLE 3

| Sample No. | Sensitivity | Contrast | Dot quality | Black spot | Note |
|---|---|---|---|---|---|
| 1 | 100 | 3.7 | 1 | 5 | Comparative |
| 2 | 120 | 13.6 | 2 | 2 | Comparative |
| 3 | 122 | 15.9 | 3 | 1 | Comparative |
| 4 | 101 | 3.6 | 1 | 4 | Comparative |
| 5 | 102 | 3.7 | 1 | 3 | Comparative |
| 6 | 105 | 4.1 | 1 | 4 | Comparative |
| 7 | 105 | 5.5 | 2 | 3 | Comparative |
| 8 | 114 | 13.9 | 4 | 4 | The present invention |
| 9 | 118 | 14.2 | 4 | 3 | The present invention |
| 10 | 123 | 13.8 | 3 | 4 | The present invention |
| 11 | 125 | 15.1 | 3 | 3 | The present invention |
| 12 | 127 | 13.4 | 4 | 4 | The present invention |
| 13 | 129 | 14.5 | 4 | 4 | The present invention |
| 14 | 121 | 14.4 | 2 | 2 | Comparative |
| 15 | 126 | 15.0 | 3 | 1 | Comparative |
| 16 | 108 | 4.6 | 1 | 3 | Comparative |
| 17 | 108 | 5.2 | 2 | 3 | Comparative |
| 18 | 122 | 14.2 | 4 | 4 | The present invention |
| 19 | 125 | 14.9 | 4 | 3 | The present invention |
| 20 | 127 | 14.5 | 4 | 4 | The present invention |
| 21 | 130 | 15.8 | 4 | 4 | The present invention |
| 22 | 131 | 15.2 | 3 | 4 | The present invention |
| 23 | 120 | 14.8 | 4 | 4 | The present invention |

TABLE 4

| Sample No. | Sensitivity | Contrast | Dot quality | Note |
|---|---|---|---|---|
| 24 | 100 | 3.2 | 1 | Comparative |
| 25 | 119 | 12.2 | 2 | Comparative |
| 26 | 122 | 13.3 | 1 | Comparative |
| 27 | 101 | 3.2 | 1 | Comparative |
| 28 | 101 | 3.7 | 1 | Comparative |
| 29 | 104 | 4.2 | 1 | Comparative |
| 30 | 106 | 5.9 | 2 | Comparative |
| 31 | 116 | 11.9 | 4 | The present invention |

TABLE 4-continued

| Sample No. | Sensitivity | Contrast | Dot quality | Note |
|---|---|---|---|---|
| 32 | 119 | 13.2 | 4 | The present invention |
| 33 | 124 | 12.8 | 3 | The present invention |
| 34 | 125 | 14.9 | 3 | The present invention |
| 35 | 126 | 12.9 | 4 | The present invention |
| 36 | 125 | 13.4 | 4 | The present invention |
| 37 | 120 | 12.8 | 2 | Comparative |
| 38 | 125 | 10.5 | 1 | Comparative |
| 39 | 107 | 4.6 | 1 | Comparative |
| 40 | 108 | 6.2 | 2 | Comparative |
| 41 | 123 | 13.2 | 4 | The present invention |
| 42 | 125 | 14.5 | 4 | The present invention |
| 43 | 126 | 13.3 | 4 | The present invention |
| 44 | 128 | 15.2 | 4 | The present invention |
| 45 | 130 | 14.2 | 3 | The present invention |
| 46 | 129 | 14.8 | 4 | The present invention |

Example 2

Samples were prepared in the same manner as in Example 1 except that the pH of the developer used in Example 1 was adjusted to the values shown in Tables 5 and 6 with aqueous sodium hydroxide solution and sulfuric acid and the developing time was 40 seconds at 35° C. The samples were evaluated on the same items as in Example 1 and additionally on pepper fog. The pepper fog is ranked in five grades with 1 being very poor and 5 being substantially no pepper fog. The results are shown in Tables 5 and 6.

TABLE 5

| Sample No. | pH | Sensitivity | Contrast | Pepper fog | Dot quality | Note |
|---|---|---|---|---|---|---|
| 24 | 10.3 | 100 | 2.4 | 5 | 1 | Comparative |
|  | 10.8 | 103 | 3.4 | 4 | 1 | Comparative |
| 25 | 10.3 | 107 | 5.3 | 4 | 2 | Comparative |
|  | 10.8 | 128 | 14.1 | 1 | 1 | Comparative |
| 26 | 10.3 | 109 | 5.9 | 2 | 2 | Comparative |
|  | 10.8 | 135 | 15.2 | 1 | 1 | Comparative |
| 28 | 10.3 | 100 | 2.5 | 4 | 1 | Comparative |
|  | 10.8 | 105 | 3.4 | 3 | 1 | Comparative |
| 29 | 10.3 | 102 | 4.0 | 3 | 1 | Comparative |
|  | 10.8 | 109 | 6.2 | 3 | 2 | Comparative |
| 30 | 10.3 | 104 | 4.3 | 3 | 1 | Comparative |
|  | 10.8 | 110 | 6.8 | 2 | 2 | Comparative |
| 31 | 10.3 | 111 | 11.7 | 4 | 3 | The present invention |
|  | 10.8 | 119 | 12.7 | 4 | 4 | The present invention |
| 32 | 10.3 | 115 | 12.1 | 4 | 4 | The present invention |
|  | 10.8 | 122 | 13.9 | 4 | 4 | The present invention |
| 33 | 10.3 | 124 | 13.6 | 4 | 4 | The present invention |
|  | 10.8 | 132 | 13.9 | 3 | 4 | The present invention |

TABLE 6

| Sample No. | pH | Sensitivity | Contrast | Pepper fog | Dot quality | Note |
|---|---|---|---|---|---|---|
| 34 | 10.3 | 124 | 14.3 | 4 | 3 | The present invention |
|  | 10.8 | 129 | 15.2 | 4 | 4 | The present invention |
| 35 | 10.3 | 124 | 12.6 | 4 | 3 | The present invention |
|  | 10.8 | 131 | 13.1 | 4 | 4 | The present invention |
| 36 | 10.3 | 124 | 13.8 | 4 | 3 | The present invention |
|  | 10.8 | 128 | 14.2 | 4 | 4 | The present invention |
| 37 | 10.3 | 112 | 7.5 | 3 | 2 | Comparative |
|  | 10.8 | 126 | 14.6 | 1 | 2 | Comparative |
| 38 | 10.3 | 115 | 11.5 | 2 | 2 | Comparative |
|  | 10.8 | 137 | 15.9 | 1 | 2 | Comparative |
| 39 | 10.3 | 107 | 5.2 | 4 | 2 | Comparative |
|  | 10.8 | 112 | 6.9 | 3 | 1 | Comparative |
| 40 | 10.3 | 109 | 5.6 | 4 | 1 | Comparative |
|  | 10.8 | 115 | 7.0 | 4 | 1 | Comparative |
| 41 | 10.3 | 122 | 13.1 | 4 | 3 | The present invention |
|  | 10.8 | 127 | 14.6 | 4 | 4 | The present invention |
| 42 | 10.3 | 124 | 13.2 | 4 | 4 | The present invention |
|  | 10.8 | 129 | 14.8 | 3 | 4 | The present invention |
| 43 | 10.3 | 124 | 13.0 | 4 | 3 | The present invention |
|  | 10.8 | 127 | 14.6 | 3 | 4 | The present invention |

TABLE 6-continued

| Sample No. | pH | Sensitivity | Contrast | Pepper fog | Dot quality | Note |
|---|---|---|---|---|---|---|
| 44 | 10.3 | 128 | 14.8 | 4 | 3 | The present invention |
|  | 10.8 | 131 | 15.5 | 4 | 4 | The present invention |
| 46 | 10.3 | 130 | 15.1 | 4 | 4 | The present invention |
|  | 10.8 | 135 | 16.8 | 3 | 3 | The present invention |

Example 3

A cubic chlorobromide emulsion (80 mol % chloride) having cubic grains with an edge length of 0.21 μm was prepared in the presence of rhodium salt using pAg-controlled double jet precipitation. After removal of the soluble salts by flocculation, the content of gelatin was controlled to 55 g per mol of Ag and sensitization was conducted with potassium thiotosylate, potassium thiosulfate and gold salt. After sensitization, there were added 1.6 millimol/mol Ag of potassium iodide, 0.12 millimol of bromine salt of cation in Compound H-11, phenyl mercaptotetrazole, 5-nitroindazole, polyethylene latex, green sensitizer, surface active agent and 0.10 millimol of sodium dichlorohydroxytriazine per gram of gelatin. This emulsion was coated on a polyethylene terephthalate base together with an overcoat solution containing gelatin, octylphenyl diethyleneoxide sulfonate surface active agent (Triton X-200, Rohm & Haas) and additives shown in Table 5 to prepare a photographic film. The coating weight is 4.2 g/m² Ag for the emulsion and 0.9 g/m² gelatin for the overcoat.

Each of the photographic film sample was exposed through a continuous tone wedge partly covered with a halftone screen and then processed with an automatic processing machine (Duerr Graphica) using a commercially available fixing solution (DuPont CUFF). The development was conducted at 36° C. for 28 seconds using the developer of the following composition.

| Water | 500 g |
|---|---|
| Sodium bisulfite | 50 g |
| Potassium hydroxide | 27 9 |
| Sodium ethylenediaminetetraacetate | 3.7 g |
| Hydroquinone | 25 g |
| Potassium bromide | 4 g |
| Benzotriazole | 0.3 g |
| Phenylmercaptotetrazole | 0.05 g |
| 4-Hydroxymethyl-4-methyl-phenylpyrazolidinone | 1 g |

| -continued | |
|---|---|
| Boric acid | 3 g |
| Sodium hydroxide | 24 g |
| Diethyleneglycol | 40 g |

Water to one liter, pH was adjusted to 10.5 at 22° C. The sample as processed above was evaluated in accordance with the following criterion.

Minimum density (Dmin), maximum density (Dmax) and relative sensitivity (S) were respectively the values at a dot image area of 50%. The toe gradient (G1) is the value at the density of 0.1 to 0.4. The main gradient (G2) is the value at the density of 1.0 to 2.5. PQ is the visual evaluation of halftone image quality. The score of 10 for PQ indicates the dot with optimum sharpness. The score of 4 to 5 shows the dot having the limited availability equal to the sharpness obtained by use of a rapid access film containing no contrast promoter. The result is shown in Table 7.

Comparative compounds used in Example 3 are recited below.

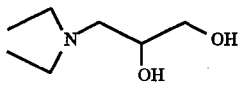
CC 4

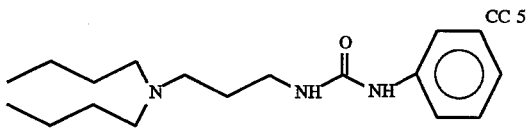
CC 5

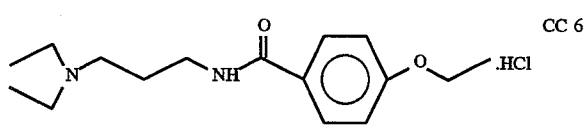
CC 6

TABLE 7

| | Additives | | | | | | | |
| Sample No. | Compound | Amount added mg/m² | Dmin | Dmax | S | G1 | G2 | PQ |
|---|---|---|---|---|---|---|---|---|
| 1 | none |  | 0.04 | 5.2 | 1.20 | 4.0 | 9.0 | 5 |
| 2 | CC-4 | 40 | 0.04 | 5.2 | 1.24 | 4.2 | 8.9 | 5 |
| 3 | CC-5 | 40 | 0.04 | 5.2 | 1.24 | 5.5 | 12 | 5 |
| 4 | CC-6 | 40 | 0.04 | 5.2 | 1.22 | 4.4 | 9 | 5 |
| 5 | A-29 | 40 | 0.04 | 5.2 | 1.38 | 7 | 18 | 8 |
| 6 | A-29 | 20 | 0.04 | 5.2 | 1.34 | 7 | 15 | 8 |

Example 4

A monodisperse silver chlorobromide emulsion with an average particle size of 0.13 μm containing $8.0 \times 10^{-6}$ mol/l mol Ag of rhodium dichloride was prepared by controlled-double jet process. After removal of the soluble salts by flocculation and washing, the redissolved emulsion was divided and to each emulsion were added respectively the hydrazine compounds and contrast promoters as shown in Table 8. Further, to each emulsion were added $5 \times 10^{-3}$ mol/l mol Ag of 5-chlorobenzotriazole and polyethylacrylate latex, sodium 2-hydroxy-4,6-dichloro-1,3,5-triazine. This emulsion was coated on a polyethyleneterephthalate film so as to give a coating weight of 3 g/m² gelatin and 5 g/m² Ag. On the coated film were further coated as a protective layer 1 g/m² gelatin and 80 mg/m² of a yellow dye having a maximum absorption wavelength at 400–450 nm (e.g. Oxonol yellow, Hoechst AG) together with surface active agent and a hardener to prepare the samples shown in Table 8. As comparative samples for the contrast promoter were used the same comparative compounds (1), (2) and (3) as recited in Example 1.

These films as prepared above were imagewise exposed through a lightroom printer (P-627FM, manufactured by Dainippon Screen Mfg. Co. Ltd.), developed with the developer shown in Example 1 at 35° C. for 30 seconds, stopped, fixed, washed and dried. For this processing was used an automatic developing machine(LD-221QT, manufactured by Dainippon Screen Mfg. Co. Ltd.). Evaluation was carried out with regard to the same items as mentioned in Example 1. The results are shown in Table 9.

TABLE 8

| Sample No. | Hydrazine compound Kind | Amount (mol/mol Ag) | Promoter Kind | Amount (g/m²) | Note |
|---|---|---|---|---|---|
| 1 | H-3 | $1 \times 10^{-3}$ | None | — | Comparative |
| 2 | H-3 | $1 \times 10^{-3}$ | Comparative compound (1) | $2 \times 10^{-2}$ | Comparative |
| 3 | H-3 | $1 \times 10^{-3}$ | Comparative compound (1) | $4 \times 10^{-2}$ | Comparative |
| 4 | H-3 | $1 \times 10^{-3}$ | Comparative compound (2) | $2 \times 10^{-2}$ | Comparative |
| 5 | H-3 | $1 \times 10^{-3}$ | Comparative compound (2) | $4 \times 10^{-2}$ | Comparative |
| 6 | H-3 | $1 \times 10^{-3}$ | Comparative compound (3) | $2 \times 10^{-2}$ | Comparative |
| 7 | H-3 | $1 \times 10^{-3}$ | Comparative compound (3) | $4 \times 10^{-2}$ | Comparative |
| 8 | H-3 | $1 \times 10^{-3}$ | A-1 | $2 \times 10^{-2}$ | The present invention |
| 9 | H-3 | $1 \times 10^{-3}$ | A-1 | $4 \times 10^{-2}$ | The present invention |
| 10 | H-3 | $1 \times 10^{-3}$ | A-3 | $2 \times 10^{-2}$ | The present invention |
| 11 | H-3 | $1 \times 10^{-3}$ | A-3 | $4 \times 10^{-2}$ | The present invention |
| 12 | H-3 | $1 \times 10^{-3}$ | A-7 | $2 \times 10^{-2}$ | The present invention |
| 13 | H-3 | $1 \times 10^{-3}$ | A-7 | $4 \times 10^{-2}$ | The present invention |
| 14 | H-12 | $1 \times 10^{-3}$ | Comparative compound (1) | $2 \times 10^{-2}$ | Comparative |
| 15 | H-12 | $1 \times 10^{-3}$ | Comparative compound (1) | $4 \times 10^{-2}$ | Comparative |
| 16 | H-12 | $1 \times 10^{-3}$ | Comparative compound (3) | $2 \times 10^{-2}$ | Comparative |
| 17 | H-12 | $1 \times 10^{-3}$ | Comparative compound (3) | $4 \times 10^{-2}$ | Comparative |
| 18 | H-12 | $1 \times 10^{-3}$ | A-1 | $2 \times 10^{-2}$ | The present invention |
| 19 | H-12 | $1 \times 10^{-3}$ | A-1 | $4 \times 10^{-2}$ | The present invention |
| 20 | H-12 | $1 \times 10^{-3}$ | A-3 | $2 \times 10^{-2}$ | The present invention |
| 21 | H-12 | $1 \times 10^{-3}$ | A-3 | $4 \times 10^{-2}$ | The present invention |
| 22 | H-12 | $1 \times 10^{-3}$ | A-13 | $2 \times 10^{-2}$ | The present invention |
| 23 | H-12 | $1 \times 10^{-3}$ | A-13 | $4 \times 10^{-2}$ | The present invention |

TABLE 9

| Sample No. | Sensitivity | Contrast | Dot quality | Black spot | Note |
|---|---|---|---|---|---|
| 1 | 100 | 5.7 | 1 | 5 | Comparative |
| 2 | 119 | 13.6 | 2 | 3 | Comparative |
| 3 | 118 | 15.9 | 2 | 2 | Comparative |
| 4 | 101 | 5.6 | 1 | 4 | Comparative |
| 5 | 101 | 5.7 | 1 | 3 | Comparative |
| 6 | 104 | 6.1 | 1 | 4 | Comparative |
| 7 | 106 | 6.5 | 2 | 3 | Comparative |
| 8 | 116 | 15.9 | 4 | 5 | The present invention |
| 9 | 119 | 16.2 | 4 | 4 | The present invention |
| 10 | 124 | 17.8 | 3 | 5 | The present invention |
| 11 | 125 | 16.1 | 3 | 4 | The present invention |
| 12 | 126 | 17.4 | 4 | 5 | The present invention |
| 13 | 125 | 17.5 | 4 | 5 | The present invention |
| 14 | 120 | 14.4 | 3 | 3 | Comparative |
| 15 | 124 | 16.0 | 3 | 2 | Comparative |
| 16 | 107 | 6.6 | 1 | 3 | Comparative |
| 17 | 108 | 6.7 | 2 | 3 | Comparative |
| 18 | 123 | 15.2 | 4 | 5 | The present invention |

TABLE 9-continued

| Sample No. | Sensitivity | Contrast | Dot quality | Black spot | Note |
|---|---|---|---|---|---|
| 19 | 125 | 15.9 | 4 | 4 | The present invention |
| 20 | 126 | 16.5 | 4 | 5 | The present invention |
| 21 | 128 | 16.8 | 4 | 4 | The present invention |
| 22 | 130 | 16.2 | 3 | 5 | The present invention |
| 23 | 129 | 16.8 | 4 | 5 | The present invention |

It can be seen that when the compounds of formulas (1) and (2) according to the present invention are used, a high contrast promoting action can be exhibited with addition of the compound in a small amount, with the improved sensitivity, contrast and dot quality. Furthermore, even when pH of the developer changes, a high contrast is maintained as compared with the comparative compounds and practically preferable photographic characteristics can be obtained with inhibiting occurrence of pepper fog. Furthermore, it is evident that when the compounds of formulas (1) and (2) are used, high contrast provided by hydrazine compounds can be produced even when a developer is used at lower pH.

In the presence of the contrast promoter selected from the present compounds of formulas (1) and (2), formation of high-contrast images using photographic silver halide materials containing hydrazine compounds can be more easily performed even with developers at lower pH as compared with the prior art, and photographic characteristics hardly affected by the change in pH can be obtained. Furthermore, the contrast promoters of the present invention can be easily synthesized and are economical and very effective.

What is claimed is:

1. A method for developing a photographic silver halide photosensitive material which comprises developing an exposed photographic silver halide photosensitive material in the presence of at least one compound selected from the group consisting of compounds of formula (1):

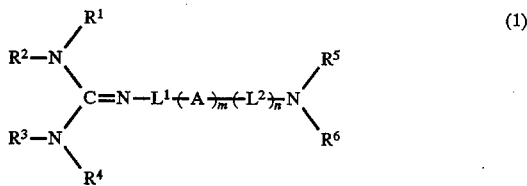

wherein $R^1$, $R^2$, $R^3$, $R^4$, $R^5$ and $R^6$ independently represent a hydrogen atom, an alkyl group, an aryl group or a heterocyclic group, $R^1$ and $R^2$, $R^3$ and $R^4$, $R^5$ and $R^6$, or $R^1$ and $R^3$, together with nitrogen atom to which they are attached, may form a ring; $L^1$ and $L^2$ independently represent an alkylene group, an arylene group or a repeated alkyleneoxy group having at least two repeated alkyleneoxy units, which groups may be substituted or unsubstituted; A represents a divalent linkage group selected from the group consisting of —$CONR^{11}$—, —$OCONR^{11}$—, —$NR^{11}COCONR^{11}$—, —$NR^{11}COO$—, —$COO$—, —$CO$—, —$NR^{11}CO$—, —$SO_2NR^{11}$—, —$NR^{11}SO_2$—, —$SO_2$—, —$O$—, —$S$—, and —$NR^{11}$—, wherein $R^{11}$ may be a hydrogen atom, an alkyl group, an acyl group or an alkylsulfonyl group; and m and n represent 0 or 1, and compounds of formula (2)

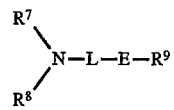

wherein $R^7$, $R^8$ and $R^9$ independently represent a hydrogen atom, an alkyl group, an aryl group or a heterocyclic group; $R^7$ and $R^8$ together with nitrogen atom to which they are attached, may form a ring; L represents an alkylene group, an arylene group or a repeated alkyleneoxy group having at least two repeated alkyleneoxy units, which groups may be substituted or unsubstituted; and E represents —$N(COR^{11})$—, —$N(CONR^{12}R^{13})$—, —$NR^{14}COCONR^{15}$—, —$N(COCONR^{16}R^{17})$—, —$N(SO_2R^{18})$— or —$N(COOR^{19})$—, where $R^{11}$—$R^{19}$ independently represent a hydrogen atom, an alkyl group, an aryl group or a heterocyclic group; and $R^{12}$ and $R^{13}$ or $R^{16}$ and $R^{17}$ together with nitrogen atom to which they are attached, may form a ring, with the proviso that when E represents —$N(COR^{11})$—, —$N(CONR^{12}R^{13})$—, —$N(SO_2R^{18})$— or —$N(COOR^{19})$—, $R^9$ is not a hydrogen atom.

2. The method of claim 1 wherein the development is carried out in the presence of the compound represented by formula (1) and a hydrazine derivative.

3. The method of claim 1 wherein the development is carried out in the presence of the compound represented by formula (2) and a hydrazine derivative.

4. The method of claim 1 wherein the compound of formula (1) is incorporated in the photosensitive material.

5. The method of claim 1 wherein the compound of formula (2) is incorporated in the photosensitive material.

6. The method of claim 4 wherein the compound of formula (1) is incorporated in a silver halide emulsion layer or other hydrophilic colloid layers.

7. The method of claim 5 wherein the compound of formula (2) is incorporated in a silver halide emulsion layer or other hydrophilic colloid layers.

8. The method of claim 6 wherein the compound of formula (1) is incorporated in an amount of $1.0 \times 10^{-4}$ to $1.0 \times 10^{-1}$ mol for 1 mol of silver halide.

9. The method of claim 7 wherein the compound of formula (2) is incorporated in an amount of $1.0 \times 10^{-4}$ to $1.0 \times 10^{-1}$ mol for 1 mol of silver halide.

10. The method of claim 1 wherein the compound of formula (1) is incorporated in a developer.

11. The method of claim 1 wherein the compound of formula (2) is incorporated in a developer.

12. The method of claim 10 wherein the compound of formula (1) is $5 \times 10^{-3}$ to 0.30 mol for 1 liter of the developer.

13. The method of claim 11 wherein the compound of formula (2) is $5 \times 10^{-3}$ to 0.30 mol for 1 liter of the developer.

14. The method of claim 2 or 3 wherein the hydrazine derivative is represented by the following formula (3)

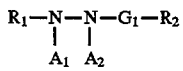
$$R_1-\underset{A_1}{N}-\underset{A_2}{N}-G_1-R_2 \qquad (3)$$

wherein $A_1$ and $A_2$ both represent hydrogen atom or one of them represents a hydrogen atom and the other represents a sulfonyl group or an acyl group, $R_1$ represents an aliphatic group, an aromatic group or a heterocyclic group, $G_1$ represents a carbonyl group, a sulfonyl group, a sulfoxy group, a phosphoryl group, an oxalyl group or an iminomethylene group, and $R_2$ represents a hydrogen atom, an aliphatic group, an aromatic group, an alkoxy group, an aryloxy group, an amino group or a group represented by the formula (4):

$$-Q^+A^- \qquad (4)$$

wherein $Q^+$ represents a group containing a cationic group and $A^-$ represents an anion and is not necessary when $Q^+$ contains a sulfo group.

15. The method of claim 2 wherein the hydrazine derivative is incorporated in a silver halide emulsion layer or other hydrophilic colloid layers.

16. The method of claim 15 wherein the hydrazine derivative is incorporated in an amount of $1\times10^{-6}$ to $1\times10^{-2}$ mol for 1 mol of silver in the silver halide emulsion.

17. A photographic silver halide photosensitive material which comprises a support and at least one silver halide emulsion layer wherein the silver halide emulsion layer or other hydrophilic colloid layers contain at least one compound selected from the group consisting of compounds of formula (1):

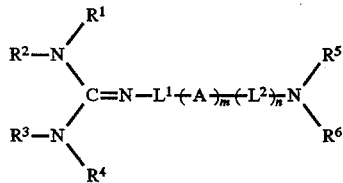

wherein $R^1$, $R^2$, $R^3$, $R^4$, $R^5$ and $R^6$ independently represent a hydrogen atom, an alkyl group, an aryl group or a heterocyclic group, $R^1$ and $R^2$, $R^3$ and $R^4$, $R^5$ and $R^6$, or $R^1$ and $R^3$, together with nitrogen atom to which they are attached, may form a ring; $L^1$ and $L^2$ independently represent an alkylene group, an arylene group or a repeated alkyleneoxy group having at least two repeated alkyleneoxy units, which groups may be substituted or unsubstituted; A represents a divalent linkage group selected from the group consisting of $-CONR^{11}-$, $-OCONR^{11}-$, $-NR^{11}COCONR^{11}-$, $-NR^{11}COO-$, $-COO-$, $-CO-$, $-NR^{11}CO-$, $-SO_2NR^{11}-$, $-NR^{11}SO_2-$, $-SO_2-$, $-O-$, $-S-$, and $-NR^{11}-$, wherein $R^{11}$ may be a hydrogen atom, an alkyl group, an acyl group or an alkylsulfonyl group; and m and n represent 0 or 1, and compounds of formula (2)

wherein $R^7$, $R^8$ and $R^9$ independently represent a hydrogen atom, an alkyl group, an aryl group or a heterocyclic group; $R^7$ and $R^8$ together with nitrogen atom to which they are attached, may form a ring; L represents an alkylene group, an arylene group or a repeated alkyleneoxy group having at least two repeated alkyleneoxy units, which groups may be substituted or unsubstituted; and E represents $-N(COR^{11})-$, $-N(CONR^{12}R^{13})-$, $-NR^{14}COCONR^{15}-$, $-N(COCONR^{16}R^{17})-$, $-N(SO_2R^{18})-$ or $-N(COOR^{19})-$, where $R^{11}-R^{19}$ independently represent a hydrogen atom, an alkyl group, an aryl group or a heterocyclic group; and $R^{12}$ and $R^{13}$ or $R^{16}$ and $R^{17}$ together with nitrogen atom to which they are attached, may form a ring, with the proviso that when E represents $-N(COR^{11})-$, $-N(CONR^{12}R^{13})-$, $-N(SO_2R^{18})-$ or $-N(COOR^{19})-$, $R^9$ is not a hydrogen atom.

* * * * *